United States Patent [19]
Iwasaki et al.

[11] Patent Number: 5,925,676
[45] Date of Patent: Jul. 20, 1999

[54] ESTER COMPOUNDS PESTICIDAL COMPOSITIONS CONTAINING THE SAME AND ITERMEDIATES FOR SYNTHESIS THEREOF

[75] Inventors: Tomonori Iwasaki; Kazunori Tsushima; Masayo Sugano, all of Sanda, Japan

[73] Assignee: Sumitomo Chemical Company, Limited, Osaka, Japan

[21] Appl. No.: 08/927,821

[22] Filed: Sep. 11, 1997

[30] Foreign Application Priority Data

Sep. 13, 1996 [JP] Japan ..................... 8-243204

[51] Int. Cl.$^6$ ................................... A01N 53/00
[52] U.S. Cl. .................. 514/531; 514/445; 514/473; 514/519; 514/521; 514/532; 558/404; 558/434; 549/66; 549/323; 560/8; 560/55; 560/105; 560/118; 560/124
[58] Field of Search .................. 560/124, 105, 560/118, 55, 8; 549/66, 323; 558/434, 404; 514/445, 473, 521, 519, 531, 532

[56] References Cited

U.S. PATENT DOCUMENTS 3,647,857   3/1972   Morgan .

FOREIGN PATENT DOCUMENTS

A-50-154420   12/1975   Japan .
A-7-330526    12/1995   Japan .

OTHER PUBLICATIONS

Padwa et al., Thermal and Solvolytic Studies with the 2–Phenylbicyclo[1.1.1] pentan–2–ol System, Journal of the American Chemical Society, 92:19, (1970), pp. 5674–5681.

R. Steyn and H.Z. Sable, Studies on Cyclitols–XVI; "Conformational Analysis of Substituted Cyclopentanes, Cyclopentenes and Cyclopentene Oxides", Tetrahedron, vol. 27, (1971), pp. 4429–4447.

Rick L. Danheiser, Carlos Martinez–Davila, John M. Morin, Jr., "Synthesis of 3–Cyclopentenols by Alkoxy–Accelerated Vinylcyclopropane Rearrangement", Journal of Organic Chemistry, 45, (1980), pp. 1340–1341.

Peter J. Wagner, Kou–Chang Liu, and Y. Noguchi, "Monoradical Rearrangements of the 1,4–Biradicals Involved in Norrish Type II Photoreactions", Journal of the American Chemical Society, 103, (1981), pp. 3837–3841.

S. Collins, Yaping Hong, Mark Kataoka, and Thelam Nguyen, "A Convenient Preparation of 3–Alkylcyclopentenones from Alkylcyclopentadienes", Journal of Organic Chemistry, 55, (1990), pp. 3395–3398.

*Primary Examiner*—Michael L. Shippen
*Attorney, Agent, or Firm*—Pillsbury Madison & Sutro LLP

[57] ABSTRACT

An ester compound represented by the formula

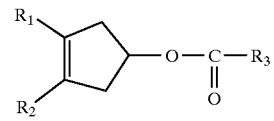

wherein $R_1$ and $R_2$ may be the same or different and each represent a $C_1$–$C_6$ alkyl group, or other specified groups, which may be optionally substituted with one or more halogen atoms; and $R_3$ represents a pyrethroid acid residue (a group resulting from elimination of the carboxyl group from pyrethroid acid), and a pesticidal composition containing the ester compound as an active ingredient.

20 Claims, No Drawings

ESTER COMPOUNDS PESTICIDAL COMPOSITIONS CONTAINING THE SAME AND ITERMEDIATES FOR SYNTHESIS THEREOF

This invention relates to novel ester compounds pesticidal compositions containing said ester compounds as an active ingredient, methods for controlling harmful arthropods by using said ester compounds and intermediates for synthesis of said ester compounds.

The novel pesticidal compounds of the present invention are ester compounds of the formula:

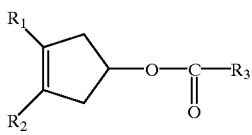

(I)

wherein $R_1$ and $R_2$ are the same or different from each other and each represent a hydrogen atom, a halogen atom (such as fluorine, chlorine, bromine, etc.), a $C_1$–$C_6$ alkyl group optionally substituted with one or more halogen atoms (such as methyl, ethyl, propyl, trifluoromethyl, difluoromethyl, 2,2,2-trifluoroethyl, chloromethyl, etc.), a $C_2$–$C_6$ alkenyl group optionally substituted with one or more halogen atoms (such as allyl, 1-methyl-2-propenyl, etc.), a $C_2$–$C_6$ alkynyl group optionally substituted with one or more halogen atoms (such as propargyl, etc.), a $C_3$–$C_7$ cycloalkyl group optionally substituted with one or more halogen atoms (such as cyclopropyl, cyclopentyl, etc.), a $C_3$–$C_7$ cycloalkenyl group optionally substituted with one or more halogen atoms (such as 2-cyclopenten-1-yl, etc.), a ($C_3$–$C_6$ cycloalkyl)methyl group optionally substituted with one or more halogen atoms (such as cyclopentylmethyl, etc.), a benzyl group optionally substituted with one or more halogen atoms (such as benzyl, 4-chlorobenzyl, 4-fluorobenzyl, etc.), a phenyl group optionally substituted with one or more halogen atoms (such as phenyl, 4-chlorophenyl, 4-fluorophenyl, etc.), or a ($C_1$–$C_6$ alkoxy)methyl group optionally substituted with one or more halogen atoms (such as methoxymethyl, ethoxymethyl, etc.); and $R_3$ represents a pyrethroid acid residue (a group resulting from elimination of the carboxyl group from pyrethroid acid).

This invention also provides alcohol compounds of the formula (II) which are useful as intermediates for synthesis in preparing some of the above-mentioned ester compounds:

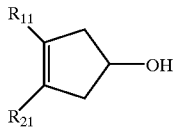

(II)

wherein $R_{11}$ represents a hydrogen atom or a $C_1$–$C_6$ alkyl group optionally substituted with one or more halogen atoms (such as methyl, ethyl, propyl, trifluoromethyl, difluoromethyl, 2,2,2-trifluoroethyl, chloromethyl, etc.); when $R_{11}$ represents a hydrogen atom, $R_{21}$ represents a $C_2$–$C_6$ alkenyl group optionally substituted with one or more halogen atoms (such as allyl, 1-methyl-2-propenyl, etc.), a $C_2$–$C_6$ alkynyl group optionally substituted with one or more halogen atoms (such as propargyl, etc.), when $R_{11}$ represents a $C_1$–$C_6$ alkyl group optionally substituted with one or more halogen atoms, $R_{21}$ represents a halogen atom (such as fluorine, chlorine, bromine, etc.), a $C_1$–$C_6$ alkyl group optionally substituted with one or more halogen atoms (such as methyl, ethyl, propyl, trifluoromethyl, difluoromethyl, 2,2,2-trifluoroethyl, chloromethyl, etc.), a $C_2$–$C_6$ alkenyl group optionally substituted with one or more halogen atoms (such as allyl, 1-methyl-2-propenyl, etc.), a $C_2$–$C_6$ alkynyl group optionally substituted with one or more halogen atoms (such as propargyl, etc.), a $C_3$–$C_7$ cycloalkyl group optionally substituted with one or more halogen atoms (such as cyclopropyl, cyclopentyl, etc.), a $C_3$–$C_7$ cycloalkenyl group optionally substituted with one or more halogen atoms, a ($C_3$–$C_6$ cycloalkyl)methyl group optionally substituted with one or more halogen atoms (such as cyclopentylmethyl, etc.), a benzyl group optionally substituted with one or more halogen atoms (such as benzyl, 4-chlorobenzyl, 4-fluorobenzyl, etc.), or a ($C_1$–$C_6$ alkoxy)methyl group optionally substituted with one or more halogen atoms (such as methoxymethyl, ethoxymethyl, etc.).

The pyrethroid acid residue, represented by $R_3$, referred to in the ester compound of this invention is not particularly limited so long as it is the residue of the carboxylic acid in an ester type pyrethroid compound and can be, for example, a group represented by the formula:

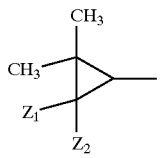

wherein $Z_1$ represents a hydrogen atom or a methyl group, and $Z_2$ represents a hydrogen atom, a $C_1$–$C_6$ alkyl group optionally substituted with one or more halogen atoms (such as methyl, etc.), a $C_1$–$C_6$ alkoxy group optionally substituted with one or more halogen atoms (such as ethoxy, propoxy, butoxy, etc.), a ($C_1$–$C_6$ alkoxy)methyl group optionally substituted with one or more halogen atoms (such as ethoxymethyl, 2,2,2-trifluoroethoxymethyl, etc.), a $C_2$–$C_4$ alkenyloxy group optionally substituted with one or more halogen atoms (such as allyloxy, etc.), a ($C_2$–$C_4$ alkenyloxy)methyl group optionally substituted with one or more halogen atoms (such as allyloxymethyl, etc.), a ($C_3$–$C_4$ alkynyloxy)methyl group optionally substituted with one or more halogen atoms (such as propargyloxymethyl, etc.), a group of the formula:

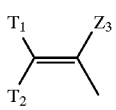

wherein $Z_3$ represents a hydrogen atom or a halogen atom, $T_1$ and $T_2$ are the same or different from each other and each represent a hydrogen atom, a halogen atom, a cyano group, a $C_1$–$C_3$ alkyl group optionally substituted with one or more halogen atoms (such as trifluoromethyl, etc.), or a phenyl group optionally substituted with one or more halogen atoms, or $T_1$ and $T_2$ conjointly represent a $(CH_2)_n$ group, wherein n is an integer of 2 to 5, (namely, ethylene, trimethylene, tetramethylene, pentamethylene), a group of the formula:

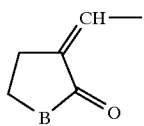

wherein B represents an oxygen atom or a sulfur atom, or a group of the formula:

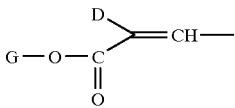

wherein D represents a hydrogen atom or a halogen atom (such as fluorine, etc.), and G represents a $C_1$–$C_6$ alkyl group optionally substituted with one or more halogen atoms (such as 1-trifluoromethyl, 2,2,2-trifluoroethyl, isopropyl, etc.), a $C_3$–$C_6$ cycloalkyl group (such as cyclopropyl, etc.), or a phenyl group optionally substituted with one or more halogen atoms.

$R_3$ can also be a group represented by the formula:

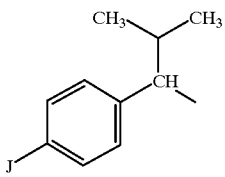

wherein J represents a halogen atom (such as chlorine, fluorine, etc.), a $C_1$–$C_6$ alkyl group optionally substituted with one or more halogen atoms (such as trifluoromethyl, difluoromethyl, etc.), or a $C_1$–$C_6$ alkoxy group optionally substituted with one or more halogen atoms (such as trifluoromethoxy, difluoromethoxy, etc.).

In the ester compounds of this invention, specific examples of the preferred pyrethroid acid residue represented by $R_3$ (the moiety resulting from elimination of the carboxyl group from the acid) include groups $Q_1$–$Q_6$ described later.

The ester compound of this invention can be prepared, for example, by the method (preparation method A) described below.

Preparation method A:

This method of preparation comprises reacting an alcohol compound represented by the formula (II')

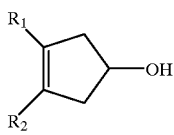

(II)' wherein $R_1$ and $R_2$ are the same as defined above, with a carboxylic acid represented by the formula (III) or its reactive derivative $R_3$—COOH  (III)

wherein $R_3$ is the same as defined above.

The reactive derivative of the carboxylic acid can be, for example, an acid halide or acid anhydride.

The reaction is preferably conducted in an inert solvent in the optional presence of an appropriate condensing agent or base.

The condensing agents which can be used include, for example, dicyclohexylcarbodiimide (DCC) and 1-ethyl-3-(3-dimethylaminopropyl)carbodiimide hydrochloride (WSC). The bases which can be used include, for example, organic bases, such as triethylamine, pyridine, 4-dimethylaminopyridine and diisopropylethylamine. The solvents which can be used include, for example, hydrocarbons, such as benzene, toluene and hexane, ethers, such as diethyl ether and tetrahydrofuran, and halogenated hydrocarbons, such as dichloromethane and 1,2-dichloroethane.

The reaction temperature can be in the range of usually from –20° C. to the boiling point of the solvent used in the reaction or to +100° C., preferably from –5° C. to the boiling point of the solvent used in the reaction or to +100° C. The molar ratio of the alcohol compound of the formula (II)' to the carboxylic acid of the formula (III) or its reactive derivative used can be selected as desired, but the reaction can advantageously conducted at an equimolar ratio or an ratio close thereto. The condensing agent or base can be used at need in an amount of 1 mole or more, preferably 1 mole to 5 moles, per mole of the alcohol compound of the formula (II)'.

After completion of the reaction, the reaction liquid can be subjected to conventional after-treatments, such as organic solvent extraction, concentration, etc. to obtain the intended compound of this invention. If necessary, the compound can be further purified by conventional operations, such as chromatography, distillation, recrystallization, etc.

The ester compounds of this invention sometimes have stereoisomers (R,S) due to an asymmetric carbon atom or geometric isomers (E, Z or cis, trans) due to a carbon-carbon double bond or cyclopropane ring. The ester compounds of this invention include all of the stereoisomers, geometrical isomers, and the mixtures thereof which have pesticidal activity.

Specific examples of the alcohol compound represented by the formula (II) include the following.
3,4-dimethyl-3-cyclopenten-1-ol
3-ethyl-4-methyl-3-cyclopenten-1-ol
3-ethyl-4-trifluoromethyl-3-cyclopenten-1-ol
3-ethyl-4-difluoromethyl-3-cyclopenten-1-ol
3-trifluoromethyl-4-methyl-3-cyclopenten-1-ol
3-difluoromethyl-4-methyl-3-cyclopenten-1-ol
3-(2,2,2-trifluoroethyl)-4-methyl-3-cyclopenten-1-ol
3-chloromethyl-4-methyl-3-cyclopenten-1-ol
3-allyl-4-methyl-3-cyclopenten-1-ol
3-allyl-4-ethyl-3-cyclopenten-1-ol
3-propargyl-4-methyl-3-cyclopenten-1-ol
3-benzyl-4-methyl-3-cyclopenten-1-ol
3-chloro-4-methyl-3-cyclopenten-1-ol
3-fluoro-4-methyl-3-cyclopenten-1-ol
3-allyl-3-cyclopenten-1-ol
3-propargyl-3-cyclopenten-1-ol
3-trifluoromethyl-3-cyclopenten-1-ol
3-difluoromethyl-3-cyclopenten-1-ol
3-(2,2,2-trifluoroethyl)-3-cyclopenten-1-ol
3-chloromethyl-3-cyclopenten-1-ol
3-(2-fluoroethyl)-3-cyclopenten-1-ol Specific examples of the alcohol compound represented by the formula (II)' include, in addition to the alcohol compounds listed above, the following compounds.
3-methyl-3-cyclopenten-1-ol 3-ethyl-3-cyclopenten-1-ol
3,4-dichloro-3-cyclopenten-1-ol
3-fluoro-3-cyclopenten-1-ol
3-chloro-3-cyclopenten-1-ol
3-bromo-3-cyclopenten-1-ol
3-benzyl-3-cyclopenten-1-ol
3-(p-chlorobenzyl)-3-cyclopenten-1-ol
3-phenyl-3-cyclopenten-1-ol
3-methoxymethyl-3-cyclopenten-1-ol
3-isopropyl-3-cyclopenten-1-ol The alcohol compound represented by the formula (II)' can be prepared, for example, according to the following reaction scheme (a), (b) or (c).

Scheme (a)

$$\underset{(IV)}{\overset{R_1}{\underset{R_2}{\diagdown}}\diagup\text{O—A}} \longrightarrow \underset{(II)'}{\overset{R_1}{\underset{R_2}{\diagdown}}\diagup\text{OH}}$$

wherein $R_1$ and $R_2$ are the same as defined above, A represents a t-butyldimethylsilyl group or a t-butyldiphenylsilyl group, t denoting tertiary (the same applies hereinafter).

The reaction shown above may usually be carried out by treating the compound (IV) with tetrabutylammonium fluoride; or an inorganic acid, such as hydrofluoric acid, hydrochloric acid and sulfuric acid; or an organic acid, such as formic acid and acetic acid. These reactants are ordinarily used in an amount of 0.5–20 moles per one mole of the compound [I]. The reaction is usually carried out in a solvent. The solvents used include, for example, ethers, such as diethyl ether and tetrahydrofuran, halogenated hydrocarbons, such as dichloromethane, hydrocarbons, such as benzene and toluene, protonic solvents, such as water, methanol and ethanol, or the mixtures thereof. The reaction temperature is usually 0° C. to 30° C. and the reaction time is usually 1 hour to 72 hours.

When a compound of the formula (II)' wherein $R_1$ or $R_2$ is a propargyl group is to be prepared, a starting compound having a 3-(trialkylsilyl)propargyl group is treated with an acid according to the above scheme (a), whereby the trialkylsilyl group is eliminated simultaneously with the elimination of the group A and the intended compound (II)' having the propargyl group is obtained.

Scheme (b)

$$\underset{(V)}{\overset{R_{12}}{\underset{R_{22}}{\diagdown}}\text{C}=\text{C}} \xrightarrow{\text{step (b-1)}}$$

$$\left[ \underset{\text{OCH}_2\text{CH}_2\text{Cl}}{\overset{R_{12}}{\underset{R_{22}}{\diagdown}}} \quad \text{or} \quad \underset{\text{OCH}_2\text{CH}_2\text{Cl}}{\overset{R_{22}}{\underset{R_{12}}{\diagdown}}} \right] \xrightarrow{\text{step (b-2)}}$$

$$\underset{(II)''}{\overset{R_{12}}{\underset{R_{22}}{\diagdown}}\diagup\text{OH}}$$

wherein $R_{12}$ and $R_{22}$ may be the same or different from each other and each represent a $C_1$–$C_6$ alkyl group, a $C_3$–$C_7$ cycloalkyl group, a $C_3$–$C_6$ cycloalkylmethyl group or a hydrogen atom.

The reaction of the step (b-1) is usually carried out by reacting the compound (V) with β-chloroethyl chloromethyl ether and lithium 2,2,6,6-tetramethylpiperidide in a solvent. The solvent used can be ethers, such as diethyl ether. The chloromethyl β-chloroethyl ether is used in an amount of usually 1–10 moles, preferably 1.5–5 moles per mole of compound (V), and the lithium 2,2,6,6-tetramethylpiperidide is used in an amount of usually 0.8–2 moles, preferably 1.0–1.5 moles per mole of compound (V). The reaction temperature is usually −78° C. to +50° C., preferably −20° C. to +30° C. The reaction time is usually 10 minutes to 10 hours.

The reaction of the step (b-2) is usually carried out by treating the reaction mixture obtained by subjecting the compound (V) to the step (b-1) with hexamethylphosphoric triamide and n-butyllithium in a solvent. The solvent used can be, for example, ethers, such as tetrahydrofuran, and hydrocarbons, such as hexane, and the mixtures thereof. The hexamethylphosphoric triamide is used in an amount of usually 2–10 moles, preferably 3–8 moles per mole of the compound (V) subjected to the step (b-1), and the n-butyllithium is used in an amount of usually 3–10 moles, preferably 5–8 moles per mole of the compound (V) subjected to the step (b-1). The reaction temperature is usually from −30° C. to +60° C., preferably from 0° C. to +50° C. The reaction time is usually from 20 minutes to 10 hours.

Scheme (c)

$$\underset{}{\text{Na}^{\oplus}\text{Cp}^{\ominus}} \xrightarrow[\text{step (c-1)}]{R_{23}\text{—X}}$$

$$\left[ \underset{}{\overset{R_{23}}{\diagup}\text{Cp}} + \underset{R_{23}}{\text{Cp}} \right] \xrightarrow[\text{step (c-2)}]{\substack{1)\ \text{disiamylborane} \\ 2)\ 3\text{ M NaOH} \\ 3)\ 30\%\ \text{H}_2\text{O}_2}}$$

$$\underset{(II)'''}{\overset{R_{23}}{\diagdown}\diagup\text{OH}}$$

wherein $R_{23}$ represents a $C_1$–$C_6$ alkyl group optionally substituted with one or more halogen atoms, a $C_2$–$C_6$ alkenyl group optionally substituted with one or more halogen atoms, a $C_2$–$C_6$ alkynyl group optionally substituted with one or more halogen atoms, a $C_3$–$C_7$ cycloalkyl group optionally substituted with one or more halogen atoms, a $C_3$–$C_7$ cycloalkenyl group optionally substituted with one or more halogen atoms, a ($C_3$–$C_6$ cycloalkyl)methyl group optionally substituted with one or more halogen atoms, a benzyl group optionally substituted with one or more halogen atoms, a phenyl group optionally substituted with one or more halogen atoms, or a ($C_1$–$C_6$ alkoxy)methyl group optionally substituted with one or more halogen atoms, and X represents a halogen atom.

The reaction of the step (c-1) can usually be carried out by reacting sodium cyclopentadienylide with a halide (iodide, bromide or chloride), the molar ratio of the former to the latter being 1:1–1:2, in an ethereal solvent, such as tetrahydrofuran, in the temperature range of from −50° C. to +30° C.

The reaction of the step (c-2) can be carried out according to the method described, for example, in J. Org. Chem., 55, 3395–3398 (1990).

The compound (IV) can be prepared, for example, by the method shown by the reaction scheme (d), (e) or (f).

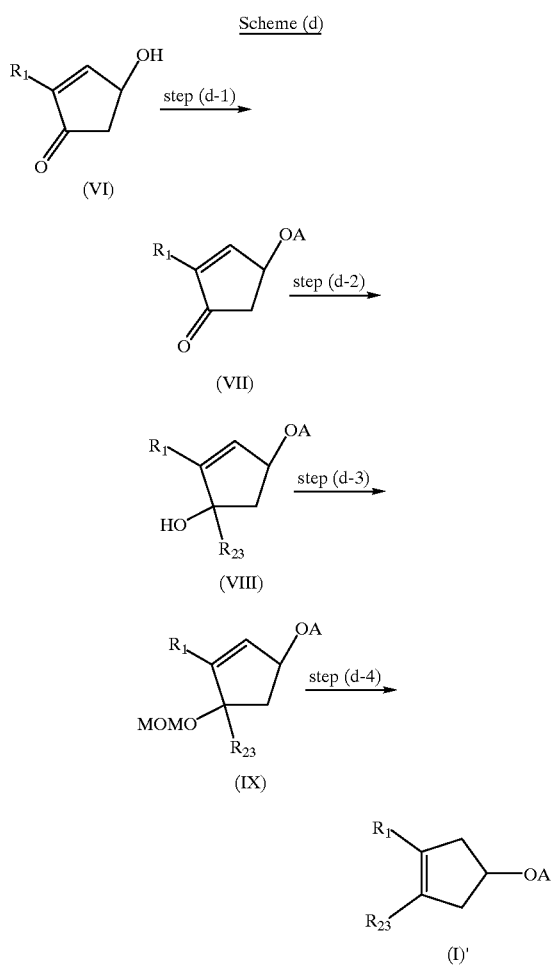

wherein $R_{23}$, $R_1$ and $R_2$ are the same as defined above.

The reaction of the step (d-1) can usually be carried out in a halogenated hydrocarbon, such as dichloromethane, an ether, such as tetrahydrofuran and diethyl ether, or an aprotic polar solvent, such as N,N-dimethylformamide, by using an organic base, such as imidazole, triethylamine, diisopropylethylamine, pyridine and 2,6-dimethylpyridine in an amount of 1–10 moles, preferably 1.2–5 moles relative to 1 mole of the compound (VI) at a temperature of −30° C. to +50° C., preferably −10° C. to +30° C., and using t-butyldimethylsilyl chloride, t-butyldiphenylsilyl chloride, t-butyldimethylsilyl triflate or t-butyldiphenylsilyl triflate in an amount of 1–2 moles, preferably 1.0–1.5 moles relative to 1 mole of the compound (VI), for a reaction time of 30 minutes to 48 hours.

The reaction of the step (d-2) can usually be carried out in an ether, such as tetrahydrofuran and diethyl ether, by using a salt represented by the formula:

$$R_{23}M$$

wherein $R_{23}$ is the same as defined above, and M represents a metal, such as lithium, magnesium and copper, particularly a lithium salt or a magnesium salt, in an amount of 0.8–5 moles, preferably 1–3 moles relative to 1 mole of the compound (VII) in the temperature range from −78° C. to +50° C., preferably −78° C. to 0° C. when a lithium salt is used and preferably −20° C. to +20° C. when a magnesium salt is used, for a reaction time of 10 minutes to 10 hours.

The reaction of the step (d-3) can usually be carried out in a halogenated hydrocarbon solvent, such as chloroform and dichloromethane, by using an organic base, such as N,N-diisopropylethylamine, in an amount of 1–10 moles, preferably 1.2–5 moles, relative to 1 mole of the compound (VIII) in a temperature range from −30° C. to +50° C., preferably −10° C. to +30° C. and using chloromethyl methyl ether in an amount of 1–3 moles, preferably 1–1.5 moles, relative to 1 mole of the compound (VIII), for a reaction time of 30 minutes to 48 hours.

The reaction of the step (d-4) can usually be carried out in a halogenated hydrocarbon solvent, such as dichloromethane, by using triethylsilane in an amount of 0.5–5 moles, preferably 1–1.5 moles, relative to 1 mole of the compound (IX) in the temperature range from −78° C. to +20° C., preferably −78° C. to 0° C., and using ethylaluminum dichloride in an amount of 0.5–2 moles, preferably 0.8–1.2 moles, relative to 1 mole of the compound (IX), for a reaction time of 5 minutes to 10 hours.

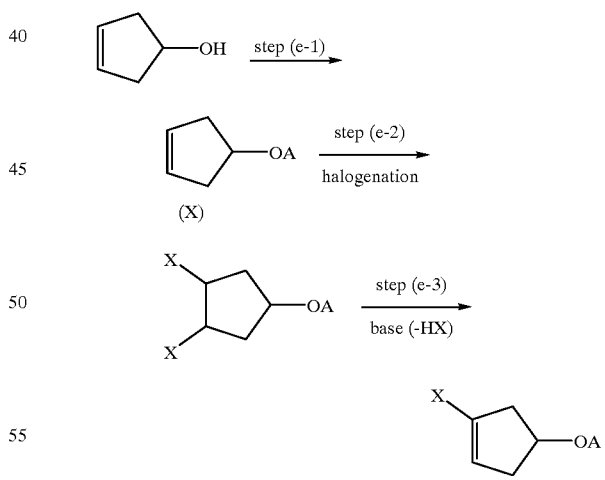

wherein A and X are the same as defined above.

The starting compound in the above scheme (e), 3-cyclopenten-1-ol, can be prepared, for example, according to the method described in J. Org. Chem., 25, 26–29 (1960).

The reaction of the step (e-1) can be conducted in the same manner as in the step (d-1) described above.

The reaction of the step (e-2) can usually be carried out by using a halogenating agent (e.g., bromine, chlorine or sulfuryl chloride) in an amount of 1–1.5 moles relative to 1 mole of the compound (X) in an inert solvent (e.g., halogenated hydrocarbon solvents, such as carbon tetrachloride and dichloromethane) in the temperature range from −50° C. to the boiling point of the solvent used.

The dehydrohalogenation in the step (e-3) can usually be carried out in an inert solvent (e.g., hydrocarbon solvents, such as benzene, toluene and hexane, halogenated hydrocarbon solvents, such as dichloromethane and carbon tetrachloride, ethers, such as 1,2-dimethoxyethane and tetrahydrofuran (THF) and alcoholic solvents, such as methanol and ethanol) in the presence of a base (e.g., alkali metal alcoholates, such as sodium methylate, sodium t-butoxide and potassium t-butoxide, tertiary amines, such as triethylamine and diazabicycloundecene (OBU), alkali metal amides, such as sodium amide, alkali metal hydroxides, such as sodium hydroxide, and alkali metal carbonates, such as potassium carbonate) in an amount of 1–10 moles, preferably 1–1.5 moles, relative to 1 mole of the compound [IX] in the temperature range from 0° C. to the boiling point of the solvent used.

The step (f-3) can be conducted according to the method described, for example, in J. Am. Chem. Soc., 106, 4630–4632 (1984).

Examples of the pests on which the ester compounds of this invention exhibit good controlling effects include harmful arthropods, e.g., insects and pests of Acarina, shown below.

Hemiptera:
  Planthoppers, such as small brown planthopper (*Laodelphax striatellus*), brown rice planthopper (*Nilaparvata lugens*) and white-backed rice planthopper (*Sogatella furcifera*); leafhoppers, such as green rice leafhopper (*Nephotettix cincticeps*), zig-zag rice leafhopper (*Recilia dorsalis*), green rice leafhopper (*Nephotettix virescens*); aphids; stink bugs; whiteflies; scales; lace bugs; psyllids; etc.

Lepidoptera:
  Pyralidae, such as rice stem borer (*Chilo suppressalis*), rice leafroller (*Cnaphalocrocis medinalis*) Indian meal moth (*Plodia interpunctella*); Noctuidae, such as

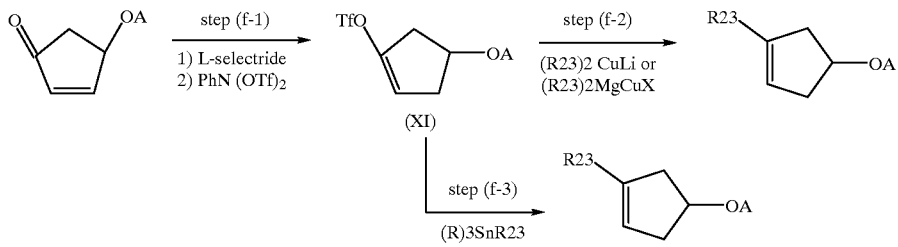

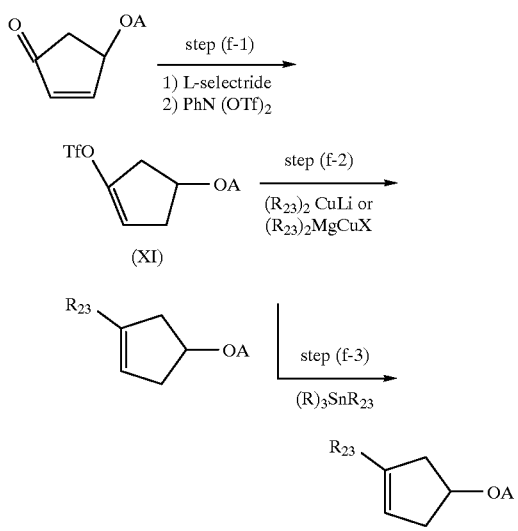

wherein A and $R_{23}$ are the same as defined above and R represents a $C_1$–$C_4$ alkyl group.

The step (f-1) can be conducted according to the method described, for example, in J. Am. Chem. Soc., 106, 7500–7506 (1984).

The step (f-2) can usually be conducted by using 1–2 equivalents of an alkylcopper reagent relative to the compound (XI) and using an ether, such as diethyl ether and THF, as a solvent in the temperature range from −78° C. to 0° C., preferably from −78° C. to −50° C.

tobacco cutworm (*Spodoptera litura*), rice armyworm (*Pseudaletia separata*), cabbage armyworm (*Mamestra brassicae*); Pieridae, such as common cabbageworm (*Pieris rapae crucivora*); Tortricidae, such as Adoxophyes spp.; Carposinidae; Lyonetiidae; Lymantriidae; Plusiinae; Agrotis spp., such as turnip moth (*Agrotis segetum*), black cutworm (*Agrotis ipsilon*); Heliothis spp.; diamondback moth (*Plutella xylostella*); casemaking clothes moth (*Tinea translucens*); webbing clothes moth (*Tineola bisselliella*); etc.

Diptera:

Culex spp., such as common mosquito (*Culex pipiens pallens*) and *Culex tritaeniorhynchus*; Aedes spp., such as *Aedes aegypti, Aedes albopictus*; Anophelinae such as *Anopheles sinensis*; Chironomidae; Muscidae, such as housefly (*Musca domestica*), false stablefly (*Muscina stabulans*) and little housefly (*Fannia canicularis*); Calliphoridae; Sarcophagidae; Anthomyiidae, such as seedcorn maggot (*Delia platura*), onion maggot (*Delia antiqua*); fruits flies (Trypediae); Drosophilidae; Psychodidae; Simuliidae; Tabanidae; stably flies (Stomoxyidae); Ceratopogonidae; etc.

Coleoptera:

Corn rootworms, such as western corn rootworm (*Diabrotica virgifera*), southern corn rootworm (*Diabrotica undecimpunctata howardi*); Scarabaeidae, such as cupreous chafer (*Anomala cuprea*) and soybeen beetle (*Anomala rufocuprea*); weevils (Curculionidae), such as maize weevil (*Sitophilus zeamais*), rice-water weevil (*Lissorhoptrus oryzophilus*); Tenebrionidae, such as yellow mealworm (*Tenebrio molitor*) and red flour beetle (*Tribolium castaneum*); leaf beetles, such as striped flea beetle (*Phyllotreta striolata*) and cucurbit leaf beetle (*Aulacophora femoralis*); Anobiidae; Epilachna spp., such as twenty-eight-spotted ladybird (*Henosepilachna vigintiocto-punctata*); powder post beetles (Lyctidae); false powder post beetles (Bostrychidae); Cerambycidae; robe beetle (*Paederus fuscipes*); etc.

Dictyoptera:

German cockroach (*Blattella germanica*), smokybrown cockroach (*Periplaneta fuliginosa*), American cockroach (*Periplaneta americana*), brown cockroach (*Periplaneta brunnea*), oriental cockroach (*Blatta orientalis*); etc.

Thysanoptera:

*Thrips plami*, flower thrips (*Thrips hawaiiensis*), etc.

Hymenoptera:

Ants; hornets; Bethylidae; Tenthredinidae, such as cabbage sawfly (*Athalia rosae ruficornis*); etc.

Orthoptera:

Gryllotalpidae, grasshoppers, etc.

Siphonaptera:

*Ctenocephalides canis, Ctenocephalides felis, Pulex irritans*, etc.

Anoplura:

*Pediculus humanus capitis, Phthirus pubis*, etc.

Isoptera:

*Reticulitermes speratus*, Formosan subterranean termite (*Coptotermes formosanus*), etc.

Tetranychidae:

Carmine spider mite (*Tetranychus cinnabarinus*), two-spotted spider mite (*Tetranychus urticae*), Kanzawa spider mite (*Tetranychus kanzawai*), citrus red mite (*Panonychus citri*), European red mite (*Panonychus ulmi*), etc.

Ixodidae:

*Boophilus microplus*, etc.

House-dust mites:

Acaridae, Dermanyssidae, Pyroglyphidae, Cheyletidae, Ornithonyssus spp., etc.

In using the ester compound of this invention as an active ingredient of pesticidal compositions, the compound is usually mixed with a solid carrier, liquid carrier, gaseous carrier or bait, or alternatively, it is usually impregnated into a base material of a mosquito coil or mat. The ester compound of this invention can be used in the form of various formulations, for example, oil formulations, emulsifiable concentrates, wettable powders, flowable formulations, such as suspension concentrates and concentrated emulsions, granules, dusts, aerosols, heating transpiratory formulations, such as mosquito coils and electrical mosquito mat and non-mat killers, heating smoking formulations, such as self combustion type smoking formulations, chemical reaction type smoking formulations and porous ceramic plate type smoking formulations, non-heating transpiratory formulations, such as resinous transpiratory formulations and impregnated paper transpiratory formulations, fogging formulations, ULV formulations and poison baits, a surfactant and other adjuvants for formulation being incorporated therein if necessary.

These formulations usually contain 0.001–95% by weight of the compound of this invention as an active ingredient.

The solid carriers used at the time of formulation include, for example, powders or granules of clays, such as kaolinite, diatomaceous earth, synthetic hydrated silicon oxide, bentonite, Fubasami clay and acid clay, talcs, ceramics, other inorganic minerals, such as sericite, quartz, sulfur, active carbon, calcium carbonate and hydrated silica, and chemical fertilizers, such as ammonium sulfate, ammonium phosphate, ammonium nitrate, urea and ammonium chloride. The liquid carriers used include, for example, water, alcohols, such as methanol and ethanol, ketones, such as acetone and methyl ethyl ketone, aromatic hydrocarbons, such as benzene, toluene, xylene, ethylbenzene and methylnaphthalene, aliphatic hydrocarbons, such as hexane, cyclohexane, kerosene and gas oil, esters, such as ethyl acetate and butyl acetate, nitriles, such as acetonitrile and isobutyronitrile, ethers, such as diisopropyl ether and dioxane, acid amides, such as N,N-dimethylformamide and N,N-dimethylacetamide, halogenated hydrocarbons, such as dichloromethane, trichloroethane and carbon tetrachloride, dimethyl sulfoxide, and vegetable oils, such as soybean oil and cotton seed oil. The gaseous carriers, i.e., propellants, include, for example, freon gas, butane gas, LPG (liquefied petroleum gas), dimethyl ether and carbon dioxide gas.

The surfactants include, for example, alkylsulfuric ester salts, alkylsulfonic acid salts, alkylarylsulfonic acid salts, alkyl aryl ethers and the polyoxyethylenated products thereof, polyethylene glycol ethers, polyhydric alcohol esters and sugar alcohol derivatives.

The adjuvants for formulation as sticking agents, dispersing agents, etc. include, for example, casein, gelatin, polysaccharides, such as starch powder, gum arabic, cellulose derivatives and alginic acid, lignin derivatives, bentonite, sugars and synthetic water-soluble polymers, such as poly(vinyl alcohol), poly(vinylpyrrolidone) and poly(acrylic acid). The stabilizers include, for example, PAP (isopropyl acid phosphate), BHT (2,6-di-tert-butyl-4-methylphenol), BHA (a mixture of 2-tert-butyl-4-methoxyphenol and 3-tert-butyl-4-methoxyphnol), vegetable oils, mineral oils, surfactants, fatty acids and their esters.

The base material for mosquito coils include, for example, mixtures of vegetable raw powders, such as wood flour and sake lees powder with binders, such as tabu powder, starch and gluten.

The base materials for electrical mosquito mats include, for exmaple, products obtained by compressing the fibrils of cotton linter or of the mixture of cotton linter and pulp into the form of solid plate.

The base materials for self-combustion type smoking formulations include, for example, combustive heat-generating agents, such as nitrates, nitrites, guanidine salts, potassium perchlorate, nitrocellulose, ethyl cellulose and wood flour, heat decomposition stipulators, such as alkali metal salts, alkaline earth metal salts, bichromates and chromates, oxygen suppliers, such as pottasium nitrate, combustion sustaining agents, such as melamine and wheat starch, extenders, such as diatomaceous earth, and binders, such as synthetic adhesive pastes.

The base materials for chemical reaction type smoking formulations may be, for example, heat generating agents, such as alkali metal sulfides, polysulfides, hydrosulfides and hydrated salts, and calcium oxide, catalytic agents, such as carbonaceous material, iron carbide and active clay, organic foaming agents, such as azodicarbonamide, benzenesulfonyl hydrazide, N,N'-dinitrosopentamethylenetetramine, polystyrene and polyurethane, and fillers, such as natural fiber chips and synthetic fiber chips.

The base materials for non-heating transpiratory formulations include, for example, thermoplastic resins, filter paper and Japanese paper.

The base materials for poison baits may be, for example, food components, such as grain powders, vegetable oils, sugars and crystalline cellulose, antioxidants, such as dibutylhydroxytoluene and nordihydroguaiaretic acid, preservatives, such as dehydroacetic acid, mis-eating preventive agents, such as red pepper powder, and attractants, such as cheese flavor, onion flavor and peanut oil.

The flowable formulations (suspension concentrates or concentrated emulsions) can be prepared, in general, by finely dispersing 1–75 parts of the compound of this invention into water containing 0.5–15 parts of a dispersing agent, 0.1–10% of a suspension aid (for example, a protective colloid or a compound which imparts thixotropy) and 0–10 parts of appropriate adjuvants (for example, antifoaming agents, anticorrosive agents, stabilizers, spreaders, permeation aids, antifreezing agents, fungi preventives and mold preventives). It is also possible to form suspension-in-oil formulations by using an oil which poorly dissolves the compound in place of water. The protective colloids used include, for example, gelatin, casein, gums, cellulose ether and poly(vinyl alcohol). The compounds which impart thixotropy include, for example, bentonite, aluminum magnesium silicate, xanthan gum and poly(acrylic acid).

The formulations thus obtained can be used as they are or after diluted with water or other suitable diluents. They can also be used as mixtures with other insecticedes, acaricides, nematicides, soil insect pest controlling agents, fungicides, herbicides, plant growth regulating agents, synergists, fertilizers and soil conditioners, or they can be used simultaneously therewith without previous mixing.

Examples of the insecticides, nematicides and acaricides which can be used include: organophosphorus compounds, such as fenitrothion [O,O-dimethyl O-(3-methyl-4-nitrophenyl)phosphorothioate], fenthion [O,O-dimethyl O-(3-methyl-4-(methylthio)phenyl) phosphorothioate], diazinon [O,O-diethyl O-2-isopropyl-6-methylpyrimidin-4-yl phosphorothioate], chlorpyrifos [O,O-diethyl O-3,5,6-trichloro-2-pyridyl phosphorothioate], acephate [0,S-dimethyl acetylphosphoramidothioate], methidathion [S-2,3-dihydro-5-methoxy-2-oxo-1,3,4-thiadiazol-3-ylmethyl O,O-dimethyl phosphorodithioate], disulfoton [O,O-diethyl S-2-ethylthioethyl phosphorodithioate], DDVP [2,2-dichlorovinyl dimethyl phosphate], sulprofos [O-ethyl O-4-(methylthio)phenyl S-propyl phosphorodithioate], cyanophos [O-4-cyanophenyl O,O-dimethyl phosphorothioate], dioxabenzofos [2-methoxy- 4H-1,3,2-benzodioxaphosphorine 2-sulfide], dimethoate [O,O-dimethyl S-methylcarbamoylmethyl phosphorodithioate], phenthoate [ethyl 2-dimethoxyphosphinothioylthio(phenyl) acetate], malathion [diethyl(dimethoxyphosphinothioylthio) succinate], trichlorfon [dimethyl 2,2,2-trichloro-1-hydroxyethylphosphonate], azinphosmethyl [S-3,4-dihydro-4-oxo-1,2,3-benzotriazin-3-ylmethyl O,O-dimethyl phosphorodithioate], monocrotophos [dimethyl (E)-1-methyl-2-(methylcarbamoyl)vinyl phosphate] and ethion [O,O,O',O'-tetraethyl S,S'-ethylene bis (phosphorodithioate)]; carbamate compounds, such as BPMC [2-sec-butylphenyl methylcarbamate], benfuracarb [ethyl N-[2,3-dihydro-2,2-dimethylbenzofuran-7-yloxycarbonyl(methyl)aminothio]-N-isopropyl-β-alaninate], propoxur [2-isopropoxyphenyl N-methylcarbamate], carbosulfan [2,3-dihydro-2,2-dimethyl-7-benzo[b]furanyl N-dibutylaminothio-N-methylcarbamate], carbaryl [1-naphthyl N-methylcarbamate], methomyl [S-methyl N-[(methylcarbamoyl)oxy]thioacetimidate], ethiofencarb [2-(ethylthiomethyl)phenyl methylcarbamate], aldicarb [2-methyl-2-(methylthio)propionaldehyde O-methylcarbamoyloxime], oxamyl [N,N-dimethyl-2-methylcarbamoyloxyimino-2-(methylthio)acetamide], and phenothiocarb [S-4-phenoxybutyl N,N-dimethylthiocarbamate]; pyrethroid compounds, such as etofenprox [2-(4-ethoxyphenyl)-2-methylpropyl 3-phenoxybenzyl ether], fenvalerate [(RS)-a-cyano-3-phenoxybenzyl (RS)-2-(4-chlorophenyl)-3-methylbutyrate], esfenvalerate [(S)-α-cyano- 3-phenoxybenzyl (S)-2-(4-chlorophenyl)-3-methylbutyrate], fenpropathrin [(RS)-α-cyano-3-phenoxybenzyl 2,2,3,3-tetramethylcyclopropanecarboxylate], cypermethrin [(RS)-α-cyano-3-phenoxybenzyl (1RS)-cis,trans-3-(2,2-dichlorovinyl)-2,2-dimethylcyclopropanecarboxylate], permethrin [3-phenoxybenzyl (1RS)-cis,trans-3-(2,2-dichlorovinyl)-2,2-dimethylcyclopropanecarboxylate], cyhalothrin [(RS)-α-cyano-3-phenoxybenzyl (Z)-(1RS)-cis-3-(2-chloro-3,3,3-trifluoroprop-1-enyl-2,2-dimethylcyclopropanecarboxylate], deltamethrin [(S)-α-cyano-3-phenoxybenzyl (1R)-cis-3-(2,2-dibromovinyl)-2,2-dimethylcyclopropanecarboxylate], cycloprothrin [(RS)-α-cyano-3-phenoxybenzyl (RS)-2,2-dichlorovinyl-1-(4-ethoxyphenyl)cyclopropanecarboxylate], fluvalinate [α-cyano-3-phenoxybenzyl N-(2-chloro-α, α, α-trifluoro-p-tolyl)-D-valinate], biphenthrin [2-methylbiphenyl-3-ylmethyl (Z)-(1RS)-cis-3-(2-chloro-3,3,3-trifluoroprop-1-enyl-2,2-dimethylcyclopropanecarboxylate], 2-methyl-2-(4-bromodifluoromethoxyphenyl)propyl (3-phenoxybenzyl) ether, tralomethrin [(S)-α-cyano-3-phenoxybenzyl (1R,cis)-3-[(RS)-1,2,2,2-tetrabromoethyl]-2,2-dimethylcyclopropanecarboxylate], silafluofen [4-ethoxyphenyl [3-(4-fluoro-3-phenoxyphenyl)propyl] dimethylsilane], d-phenothrin [3-phenoxybenzyl (1R-cis, trans)-chrysanthemate], cyphenothrin [(RS)-α-cyano-3-phenoxybenzyl (1R-cis,trans)chrysanthemate], d-resmethrin [5-benzyl-3-furylmethyl (1R-cis,trans)chrysanthemate], acrinathrin [(S)-α-cyano-3-phenoxybenzyl (1R-cis(Z))-2,2-dimethyl- 3-[3-oxo-3-(1,1,1,3,3,3-hexafluoropropyloxy)-propenyl]cyclopropanecarboxylate], cyfluthrin [(RS)-α-cyano-4-fluoro-3-phenoxybenzyl 3-(2,2-dichlorovinyl)-2,2-dimethylcyclopropanecarboxylate], tefluthrin [2,3,5,6-tetrafluoro-4-methylbenzyl (1RS-cis(Z))-3-(2-chloro-3,3,3-trifluoroprop-1-enyl)-2,2-dimethylcyclopropanecarboxylate], transfluthrin [2,3,5,6-tetrafluorobenzyl (1R-trans)-3-(2,2-dichlorovinyl)-2,2-dimethylcyclopropanecarboxylate], tetramethrin [3,4,5,6-tetrahydrophthalimidomethyl (1RS)-cis,trans-chrysanthemate], allethrin [(RS)-3-allyl-2-methyl-4-oxocyclopent-2-enyl (1RS)-cis ,trans-chrysanthemate], prallethrin [(S)-2-methyl-4-oxo-3-(2-propynyl)cyclopent-2-enyl (1R)-cis,trans-chrysanthemate], empenthrin [(RS)-1-ethynyl-2-methyl-2-pentenyl (1R)-cis,trans-chrysanthemate], imiprothrin [2,5-dioxo-3-(prop-2-ynyl) imidazolidin-1-ylmethyl (1R)-cis,trans-2,2-dimethyl-3-(2-methylprop-1-enyl)cyclopropanecarboxylate], d-furamethrin [5-(2-propynyl)furfuryl (1R)-cis,trans-chrysanthemate], 5-(2-propynyl)furfuryl 2,2,3,3-tetramethylcyclopropanecarboxylate; thiadiazine compounds, such as buprofezin [2-tert-butylimino-3-isopropyl-5-phenyl-1,3,5-thiadiazinan-4-one]; nitroimidazolidine compounds, such as imidacloprid [1-(6-chloro-3-pyridylmethyl)-N-nitroimidazolidin-2-ylideneamine]; nereistoxin derivatives, such as cartap [S,S'-(2-dimethylaminotrimethylene)bis (thiocarbamate), thiocyclam [N,N-dimethyl-1,2,3-trithian-5-ylamine], and bensultap [S,S'-2-dimethylaminitrimethylene di(benzenethiosulfonate)]; N-cyanoamidine compounds, such as N-cyano-N'-methyl-N'-(6-chloro-3-pyridylmethyl)-acetamidine; chlorinated hydrocarbon compounds, such as endosulfan [6,7,8,9,10,10-hexachloro-1,5,5a,6,9,9a-hexahydro-6,9-methano-2,4,3-benzodioxathiepine 3-oxide], γ-BHC [1,2,3,4,5,6-hexachlorocyclohexane] and 1,1-bis(chlorophenyl)-2,2,2-trichloroethanol; benzoylurea compounds, such as chlorfluazuron [1-(3,5-dichloro-4-(3-chloro-5-trifluoromethylpyridin-2-yloxy)phenyl)-3-(2,6-difluorobenzoyl)urea], teflubenzuron [1-(3,5-dichloro-2,4-difluorophenyl)-3-(2,6-difluorobenzoyl)urea] and flufenoxuron [1-(4-(2-chloro-4-trifluoromethylphenoxy)-2-fluorophenyl)-3-(2,6-difluorobenzoyl)urea]; formamidine derivatives, such as amitraz [N-methylbis(2,4-xylyliminomethyl)amine] and chlordimeform [N'-(4-chloro-2-methylphenyl)-N,N-dimethylmethanimidamide]; thiourea compounds, such as diafenthiuron [N-(2,6-diisopropyl-4-phenoxyphenyl)-N'-tert-butylthiourea; arylpyrazole compounds; metoxadiazone [5-methoxy-3-(2-methoxyphenyl)-1,3,4-oxadiazol-2(3H)one]; bromopropylate [isopropyl 4,4'-dibromobenzilate]; tetradifon [4-chlorophenyl 2,4,5-trichlorophenyl sulfone]; chinomethionat [S,S-(6-methylquinoxalin-2,3-diyl) dithiocarbonate]; propargite [2-(4-tert-butylphenoxy)cyclohexyl prop-2-yl sulfite; fenbutatin oxide [bis(tris(2-methyl-2-phenylpropyl)-tin) oxide]; hexythiazox [(4RS,5RS)-5-(4-chlorophenyl)-N-cyclohexyl-4-methyl-2-oxo-1,3-thiazolidine-3-carboxamide]; clofentezine (3,6-bis(2-chlorophenyl)-1,2,4, 5-tetrazine]; pyridaben [2-tert-butyl-5-(4-tert-butylbenzylthio)-4-chloropyridazin-3(2H)-one]; fenpyroximate [tert-butyl (E)-4-((1,3-dimethyl-5-phenoxypyrazol-4-yl)methyleneaminooxymethyl) benzoate]; tebufenpyrad [N-(4-tert-butylbenzyl)-4-chloro-3-ethyl-1-methylpyrazole-5-carboxamide]; polynactin complex [tetranactin, dinactin, trinactin]; pyrimidifen [5-chloro-N-(2-(4-(2-ethoxyethyl)-2,3-dimethylphenoxy)-ethyl)-6-ethylpyrimidin-4-amine]; milbemectin; abamectin; ivermectin; and azadirachtin [AZAD].

When the compound of this invention is used as an active ingredient of pesticidal compositions for agricultural use, the amount of the compound to be applied is usually 5–500 g per 10 ares. When the compound of this invention is used as an active ingredient of emulsifiable concentrates, wettable powders, flowable formulations, etc., these formulations are used after diluted with water so that the concentration of the compound at the time of application is usually 0.1–1000 ppm. Granules, dusts, resinous formulations and the like containing the compound of this invention as an active ingredient are used as they are without any dilution. When the compound is used as an active ingredient of pesticidal compositions for household or public hygiene or for animals, the emulsifiable concentrates, wettable powders, flowable formulations and the like containing the compound of this invention as an active ingredient are usually applied after diluted with water so as to have an active ingredient concentration of 0.1–10,000 ppm, and the oil formulations, aerosols, fumigants, smoking formulations, transpiratory formulations, fogging formulations, ULV formulations, resinous formulations, poison baits and the like containing the compound of this invention are applied as they are.

EXAMPLE 1

To a mixture of (RS)-3-ethyl-4-methyl-3-cyclopenten-1-ol (115 mg), 2,6-di-tert-butyl-4-methylphenol (5 mg), pyridine (92 mg) and toluene (10 ml), (1RS)-cis-3-(Z-2-chloro-3,3,3-trifluoro-1-propenyl)-2,2-dimethylcyclopropanecarbonyl chloride (238 mg) was added under ice-cooling. The resulting reaction mixture was further allowed to react for 8 hours at room temperature. Then the reaction mixture was poured into ice-cooled 5% aqueous solution of citric acid and extracted three times with diethyl ether. After the combined ether layer was washed successively with saturated sodium bicarbonate solution and saturated sodium chloride solution and dried over anhydrous magnesium sulfate, the solvent was evaporated under reduced pressure. The obtained residue was subjected to silica gel column chromatography (eluent; n-hexane/ethyl acetate=30/1) to afford 265 mg of (RS)-3-ethyl-4-methyl-3-cyclopenten-1-yl (1RS)-cis-3-(Z-2-chloro-3,3,3-trifluoro-1-propenyl)-2,2-dimethylcyclopropanecarboxylate (Compound No. 11). Yield 83% $n_D^{27}$ 1.4645

$^1$H-NMR (CDCl$_3$, internal standard TMS) δ value (ppm) 0.99 (t,3H), 1.30 (s,6H), 1.68 (s,3H), 1.97 (d,1H), 2.03–2.42 (m,5H), 2.69–2.87 (m,2H), 5.21–5.39 (m,1H), 6.91–7.05 (m,1H)

EXAMPLE 2

To a mixture of 3,4-dimethyl-3-cyclopenten-1-ol (175 mg), 2,6-di-tert-butyl-4-methylphenol (5 mg), pyridine (150 mg) and toluene (10 ml), (1RS)-cis-3-(Z-2-chloro-3,3,3-trifluoro-1-propenyl)-2,2-dimethylcyclopropanecarbonyl chloride (395 mg) was added under ice-cooling. The resulting reaction mixture was further allowed to react for 8 hours at room temperature. Then the reaction mixture was subjected to the same post-treatment as in Example 1 to afford 441 mg of 3,4-dimethyl-3-cyclopenten-1-yl (1RS)-cis-3-(Z-2-chloro-3,3,3-trifluoro-1-propenyl)-2,2-dimethylcyclopropanecarboxylate (Compound No. 3). Yield 84% $n_D^{25}$ 1.4620

$^1$H-NMR (CDCl$_3$, internal standard TMS) δ value (ppm) 1.29 (s,6H), 1.62 (s,6H), 1.98 (d,1H), 2.11 (t,1H), 2.20–2.35 (m,2H), 2.65–2.81 (m,2H), 5.22–5.30 (m,1H), 6.95 (dd,1H)

EXAMPLE 3

To a mixture of (RS)-3-(2-propenyl)-4-methyl-3-cyclopenten- 1-ol (190 mg), 2,6-di-tert-butyl-4-methylphenol (5 mg), pyridine (140 mg) and toluene (10 ml), (1R)-trans-2,2-dimethyl-3-(2-methyl-1-propenyl)-cyclopropanecarbonyl chloride was added under ice-cooling. The resulting reaction mixture was further allowed to react for 8 hours at room temperature. Then the reaction mixture was subjected to the same post-treatment as in Example 1 to afford 295 mg of (RS)-3-(2-propenyl)-4-methyl-3-cyclopenten-1-yl (1R)-trans-2,2-dimethyl-3-(2- methyl-1-propenyl)cyclopropanecarboxylate (Compound No. 40). Yield 74% $n_D^{25}$ 1.4891

$^1$H-NMR (CDCl$_3$, internal standard TMS) δ value (ppm) 1.12 (s,3H), 1.28 (d,3H), 1.39 (d,1H), 1.58 s,3H), 1.71 (d,6H), 2.08 (t,1H), 2.28–2.42 (m,1H), 2.66–2.88 (m,3H), 4.91 (s,1H), 4.92–5.08 (m,2H), 5.21–5.30 (m,1H), 5.78–5.85 (m,1H)

EXAMPLE 4

To a mixture of (RS)-3-(2-propenyl)-4-methyl-3-cyclopenten-1-ol (190 mg), 2,6-di-tert-butyl-4-methylphenol (5 mg), pyridine (140 mg) and toluene (10 ml), (1RS)-cis-3-(Z-2-chloro-3,3,3-trifluoromethyl-1-propenyl)-2,2-dimethylcyclopropanecarbonyl chloride (353 mg) was added under ice-cooling. The resulting reaction mixture was further allowed to react for 8 hours at room temperature. Then the reaction mixture was subjected to the same post-treatment as in Example 1 to afford 382 mg of (RS)-3-(2-propenyl)-4-methyl-3-cyclopenten-1-yl (1RS)-cis-3-(Z-2-chloro-3,3,3-trifluoromethyl-1-propenyl)-2,2-dimethylcyclopropanecarboxylate (Compound No. 34). Yield 77% $n_D^{24}$ 1.4721

$^1$H-NMR (CDCl$_3$, internal standard TMS) δ value (ppm) 1.30 (s,6H), 1.68 (s,3H), 1.98 (d,1H), 2.15 (t,1H), 2.25–2.40 (m,1H), 2.65–2.99 (m,3H), 4.98–5.10 (m,2H), 5.21–5.31 (m,1H), 5.68–5.82 (m,1H), 6.97 (dd,1H).

EXAMPLE 5

To a mixture of (RS)-3,4-dimethyl-3-cyclopenten-1-ol (175 mg), 2,6-di-tert-butyl-4-methylphenol (5 mg), pyridine (150 mg) and toluene (10 ml), (1R)-trans-2,2-dimethyl-3-(2,2-dichlorovinyl)cyclopropanecarbonyl chloride (344 mg) was added under ice-cooling. The resulting reaction mixture was further allowed to react for 8 hours at room temperature. Then the reaction mixture was subjected to the same post-treatment as in Example 1 to afford 379 mg of (RS)-3,4-dimethyl-3-cyclopenten-1-yl (1R)-trans-2,2-dimethyl-3-(2,2-dichlorovinyl)cyclopropanecarboxylate (Compound No. 106). Yield 80% $n_D^{25}$ 1.5041

$^1$H-NMR (CDCl$_3$, internal standard TMS) δ value (ppm) 1.18 (s,3H), 1.29 (s,3H), 1.60 (d,1H), 1.62 (s,6H), 2.16–2.39 (m,3H), 2.62–2.80 (m,2H), 5.22–5.31 (m,1H), 5.60 (d,1H)

EXAMPLE 6

To a mixture of (RS)-3-(2-propenyl)-4-methyl-3-cyclopenten-1-ol (190 mg), 2,6-di-tert-butyl-4-methylphenol (5 mg), pyridine (140 mg) and toluene (10 ml), (1R)-trans-2,2-dimethyl-3-(2,2-dichlorovinyl) cyclopropanecarbonyl chloride (310 mg) was added under ice-cooling. The resulting reaction mixture was further allowed to react for 8 hours at room temperature. Then the reaction mixture was subjected to the same post-treatment as in Example 1 to afford 379 mg of (RS)-3-(2-propenyl)-4-methyl-3-cyclopenten-1-yl (1R)-trans-2,2-dimethyl-3-(2,2-dichlorovinyl)cyclopropanecarboxylate (Compound No. 18). Yield 77% $n_D^{24}$ 1.5112

$^1$H-NMR (CDCl$_3$, internal standard TMS) δ value (ppm) 1.19 (s,3H), 1.29 (d,3H), 1.57 (d,1H), 1.68 (s,3H), 2.22 (dt,1H), 2.27–2.42 (m,1H), 2.68–2.86 (m,3H), 4.96–5.09 (m,2H), 5.21–5.32 (m,1H), 5.51 (d,1H), 5.18–5.32 (m,1H)

EXAMPLE 7

To a mixture of (RS)-3,4-dimethyl-3-cyclopenten-1-ol (655 mg), 2,6-di-tert-butyl-4-methylphenol (5 mg), pyridine (585 mg) and toluene (10 ml), (1R)-trans-3-(Z-2-chloro-3,3,3-trifluoro-1-propenyl)-2,2-dimethylcyclopropanecarbonyl chloride (1.5 g) was added under ice-cooling. The resulting reaction mixture was further allowed to react for 8 hours at room temperature. Then the reaction mixture was subjected to the same post-treatment as in Example 1 to afford 1.76 g of (RS)-3,4-dimethyl-3-cyclopenten-1-yl (1R)-trans-3-(Z-2-chloro-3,3,3-trifluoro-1-propenyl)-2,2-dimethylcyclopropanecarboxylate (Compound No. 30). Yield 90% $n_D^{23}$ 1.4651

$^1$H-NMR (CDCl$_3$, internal standard TMS) δ value (ppm) 1.25 (s,3H), 1.38 (s,3H), 1.68 (s,6H), 1.79 (d,1H), 2.22–2.49 (m,3H), 2.68–2.85 (m,2H), 5.25–5.38 (m,1H), 6.18 (dd,1H)

EXAMPLE 8

To a mixture of (RS)-3-(2-propenyl)-3-cyclopenten-1-ol (115 mg), 2,6-di-tert-butyl-4-methylphenol (5 mg), pyridine (100 mg) and toluene (10 ml), (IRS)-cis-3-(Z-2-chloro-3,3,3-trifluoro-1-propenyl)-2,2-dimethylcyclopropanecarbonyl chloride (239 mg) was added under ice-cooling. The resulting reaction mixture was further allowed to react for 8 hours at room temperature. Then the reaction mixture was subjected to the same post-treatment as in Example 1 to afford 250 mg of (RS)-3-(2-propenyl)-3-cyclopenten-1-yl (IRS)-cis-3-(Z-2-chloro-3,3,3-trifluoro-1-propenyl)-2,2-dimethylcyclopropanecarboxylate (Compound No. 35). Yield 77% $n_D^{25}$ 1.4713

$^1$H-NMR (CDCl$_3$, internal standard TMS) δ value (ppm) 1.29 (s,6H), 1.97 (d,1H), 2.13 (t,1H), 2.20–2.45 (m,2H), 2.61–2.89 (m,4H), 5.00–5.12 (m,2H), 5.31–5.42 (m,2H), 5.78–5.98 (m,1H), 6.93 (dd,1H)

EXAMPLE 9

To a mixture of (RS)-3-(2-propenyl)-3-cyclopenten-1-ol (115 mg), 2,6-di-tert-butyl-4-methylphenol (5 mg), pyridine (5 mg) and toluene (5 ml), (1R)-trans-2,2-dimethyl-3-(2-methyl-1-propenyl)cyclopropanecarbonyl chloride (171 mg) was added under ice-cooling. The resulting reaction mixture was further allowed to react for 8 hours at room temperature. Then the reaction mixture was subjected to the same post-treatment as in Example 1 to afford 165 mg of (RS)-3-(2-propenyl)-3-cyclopenten-1-yl (1R)-trans-2,2-dimethyl-3-(2-methyl-1-propenyl)cyclopropanecarboxylate (Compound No. 41). Yield 65% $D_D^{27}$ 1.4895

$^1$H-NMR (CDCl$_3$, internal standard TMS) δ value (ppm) 1.12 (s,3H), 1.28 (s,3H), 1.38 (d,1H), 1.72 (s,3H), 1.73 (s,3H), 2.05 (dd,1H), 2.22–2.45 (m,2H), 2.62–2.88 (m,4H), 4.85–4.95 (m,1H), 5.01–5.12 (m,2H), 5.31–5.45 (m,2H), 5.79–5.95 (m,1H)

EXAMPLE 10

To a mixture of (RS)-3,4-dimethyl-3-cyclopenten-1-ol (200 mg), 2,6-di-tert-butyl-4-methylphenol (5 mg), pyridine (180 mg) and toluene (10 ml), (1R)-cis-2,2-dimethyl-3-(2-methyl-1-propenyl)cyclopropanecarbonyl chloride (333 mg) was added under ice-cooling. The resulting reaction mixture was further allowed to react for 8 hours at room temperature. Then the reaction mixture was subjected to the same post-treatment as in Example 1 to afford 165 mg of (RS)-3,4-dimethyl-3-cyclopenten-1-yl (1R)-cis-2,2-dimethyl-3-(2-methyl-1-propenyl)cyclopropanecarboxylate (Compound No. 107). Yield 74% $n_D^{23}$ 1.4879

$^1$H-NMR (CDCl$_3$, internal standard TMS) δ value (ppm) 1.18 (s,3H), 1.25 (s,3H), 1.61 (s,6H), 1.62 (d,1H), 1.69 (s,3H), 1.75 (s,3H), 2.22–2.38 (m,2H), 2.62–2.79 (m,2H), 5.20–5.30 (m,1H), 5.41 (dd,1H)

EXAMPLE 11

To a mixture of (RS)-3-(2-propenyl)-3-cyclopenten-1-ol (100 mg), 2,6-di-tert-butyl-4-methylphenol (5 mg), pyridine (82 mg) and toluene (5 ml), (1R)-trans-2,2-dimethyl-3-(2,2-dichlorovinyl)cyclopropanecarbonyl chloride (181 mg) was added under ice-cooling. The resulting reaction mixture was further allowed to react for 8 hours at room temperature. Then the reaction mixture was subjected to the same post-treatment as in Example 1 to afford 145 mg of (RS)-3-(2-propenyl)-3-cyclopenten-1-yl (1R)-trans-2,2-dimethyl-3-(2,2-dichlorovinyl)cyclopropanecarboxylate (Compound No. 29). Yield 57% $n_D^{25}$ 1.5100

$^1$H-NMR (CDCl$_3$, internal standard TMS) δ value (ppm) 1.19 (s,3H), 1.29 (s,3H), 1.59 (s,1H), 2.22 (dd,1H), 2.21–2.50 (m,2H), 2.64–2.91 (m,4H), 5.00–5.12 (m,1H), 5.31–5.41 (m,1H), 5.59 (dd,1H), 5.73–5.91 (m,1H)

EXAMPLE 12

(RS)-3-benzyl-3-cyclopenten-1-ol (100 mg) was used instead of (RS)-3,4-dimethyl-3-cyclopenten-1-ol used in Example 5 above and the reaction procedures were carried out in the same manner as in Example 5 to afford 88 mg of (RS)-3-benzyl-3-cyclopenten-1-yl (1R)-trans-2,2-dimethyl-3-(2,2-dichlorovinyl)cyclopropanecarboxylate (Compound No. 49). Yield 42% $n_D^{26}$ 1.5414

$^1$H-NMR (CDCl$_3$, internal standard TMS) δ value (ppm) 1.19 (s,3H), 1.27 (d,3H), 1.57 (d,1H), 2.12–2.48 (m,3H), 2.57–2.83 (m,2H), 3.41 (brs,2H), 5.28–5.40 (m,2H), 5.59 (d,1H), 7.11–7.39 (m,5H)

EXAMPLE 13

(RS)-3-chloromethyl-3-cyclopenten-1-ol (55 mg) was used instead of (RS)-3-ethyl-4-methyl-3-cyclopenten-1-ol used in Example 1 above and the reaction procedures were carried out in the same manner as in Example 1 to afford 97 mg of (RS)-3-chloromethyl-3-cyclopenten-1-yl (1RS)-cis-3-(Z-2-chloro-3,3,3-trifluoro-1-propenyl)-2,2-dimethylcyclopropanecarboxylate (Compound No. 112). Yield 65%

$^1$H-NMR (CDCl$_3$, internal standard TMS) δ value (ppm) 1.30 (s,6H), 1.92 (d,1H), 2.12 (dd,1H), 2.32–2.51 (m,2H), 2.79–2.92 (m,2H), 4.13 (s,2H), 5.31–5.43 (m,1H), 5.71 (brs,1H), 6.98 (d,1H)

EXAMPLE 14

To a mixture of (RS)-3-allyl-3-cyclopenten-1-ol (300 mg), 2,2,3,3-tetramethylcyclopropanecarboxylic acid (343 mg), 4-dimethylaminopyridine (5 mg), triethylamine (733 mg) and dichloromethane (10 ml), 1-ethyl-3-(3-dimethylaminopropyl)carbodiimide hydrochloride (WSC) was added under ice-cooling. The resulting reaction mixture was further allowed to react for 8 hours at room temperature. Then aqueous ammonia (10 ml) was added to the reaction mixture and the reaction mixture was stirred vigorously for 2 hours. The reaction solution was extracted twice with diethyl ether. After the combined ether layer was washed with saturated sodium chloride solution and dried over anhydrous magnesium sulfate, the solvent was evaporated under reduced pressure. The obtained residue was subjected to silica gel column chromatography to afford 45 mg of (RS)-3-allyl-3-cyclopenten-1-yl 2,2,3,3-tetramethylcyclopropanecarboxylate (Compound No. 117). Yield 8%

$^1$H-NMR (CDCl$_3$, internal standard TMS) δ value (ppm) 1.18 (s,7H), 1.22 (s,6H), 2.21–2.42 (m,2H), 2.61–2.87 (m,4H), 4.98–5.12 (m,2H), 5.29–5.40 (m,2H), 5.78–5.92 (m,1H)

EXAMPLE 15

(RS)-3-propargyl-3-cyclopenten-1-ol (64 mg) was used instead of (RS)-3,4-dimethyl-3-cyclopenten-1-ol used in Example 5 above and the reaction procedures were carried out in the same manner as in Example 5 to afford 135 mg of (RS)-3-propargyl-3-cyclopenten-1-yl (1R)-trans-2,2-dimethyl-3-(2,2-dichlorovinyl)cyclopropanecarboxylate (Compound No. 10). Yield 82% $n_D^{23}$ 1.5192

$^1$H-NMR (CDCl$_3$, internal standard TMS) δ value (ppm) 1.19 (s,3H), 1.30 (s,3H), 1.58 (d,1H), 2.09 (t,1H), 2.22 (dd,1H), 2.28–2.50 (m,2H), 2.69–2.88 (m,2H), 2.99 (brs, 2H), 5.31–5.42 (m,1H), 5.56–5.68 (m,2H)

EXAMPLE 16

(RS)-3-ethyl-3-cyclopenten-1-ol (12.5 mg) was used instead of (RS)-3-ethyl-4-methyl-3-cyclopenten-1-ol used in Example 1 above and the reaction procedures were carried out in the same manner as in Example 1 to afford 30 mg of (RS)-3-ethyl-3-cyclopenten-1-yl (1RS)-cis-3-(Z-2-chloro-3,3,3-trifluoro-1-propenyl)-2,2-dimethylcyclopropanecarboxylate (Compound No. 118). Yield 80% $n_D^{21}$ 1.4629

$^1$H-NMR (CDCl$_3$, internal standard TMS) δ value (ppm) 1.06 (t,3H), 1.29 (s,6H), 1.98 (d,1H), 1.99–2.17 (m,3H), 2.21–2.43 (m,2H), 2.60–2.82 (m,2H), 5.22–5.41 (m,2H), 6.95 (d,1H)

EXAMPLE 17

(RS)-3-methyl-3-cyclopenten-1-ol (15 mg) was used instead of (RS)-3-ethyl-4-methyl-3-cyclopenten-1-ol used in Example 1 above and the reaction procedures were carried out in the same manner as in Example 1 to afford 31 mg of (RS)-3-methyl-3-cyclopenten-1-yl (1RS)-cis-3-(Z-2-chloro-3,3,3-trifluoro-1-propenyl)-2,2-dimethylcyclopropanecarboxylate (Compound No. 119). Yield 63% $n_D^{21}$ 1.4624

$^1$H-NMR (CDCl$_3$, internal standard TMS) δ value (ppm) 1.29 (s,6H), 1.75 (brd,3H), 1.94 (d,1H), 2.12 (t,1H), 2.19–2.40 (m,2H), 2.59–2.81 (m,2H), 5.25–5.39 (m,2H), 6.92 (d,1H)

EXAMPLE 18

(RS)-3-propyl-3-cyclopenten-1-ol (100 mg) was used instead of (RS)-3,4-dimethyl-3-cyclopenten-1-ol used in Example 5 above and the reaction procedures were carried out in the same manner as in Example 5 to afford 200 mg of (RS)-3-propyl-3-cyclopenten-1-yl (1R)-trans-2,2-dimethyl-3-(2,2-dichlorovinyl)cyclopropanecarboxylate (Compound No. 121). Yield 80% $n_D^{19}$ 1.5030

$^1$H-NMR (CDCl$_3$, internal standard TMS) δ value (ppm) 0.91 (t,3H), 1.18 (s,3H), 1.29 (s,3H), 1.38–1.51 (m,1H), 1.59 (d,1H), 2.04 (t,2H), 2.23–2.42 (m,2H), 2.21 (dd,1H), 2.61–2.81 (m,2H), 5.25–5.40 (m,2H), 5.59 (d,1H)

EXAMPLE 19

(RS)-3-propyl-3-cyclopenten-1-ol (400 mg) was used instead of (RS)-3-ethyl-4-methyl-3-cyclopenten-1-ol used in Example 1 above and the reaction procedures were carried out in the same manner as in Example 1 to afford 1000 mg of (RS)-3-propyl-3-cyclopenten-1-yl (1RS)-cis-3-(Z-2-chloro-3,3,3-trifluoro-1-propenyl)-2,2-dimethylcyclopropanecarboxylate (Compound No. 122). Yield 90% $n_D^{23}$ 1.4592

$^1$H-NMR (CDCl$_3$, internal standard TMS) δ value (ppm) 0.89 (t,3H), 1.29 (s,6H), 1.39–1.52 (m,2H), 1.92 (d,1H), 2.05 (t,2H), 2.13 (dd,1H), 2.20–2.42 (m,2H), 2.58–2.82 (m,2H), 5.21–5.42 (m,2H), 6.92 (d,1H)

EXAMPLE 20

(RS)-3-(2-fluoroethyl)-3-cyclopenten-1-ol (400 mg) was used instead of (RS)-3-ethyl-4-methyl-3-cyclopenten-1-ol used in Example 1 above and the reaction procedures were carried out in the same manner as in Example 1 to afford 928 mg of (RS)-3-(2-fluoroethyl)-3-cyclopenten-1-yl (1RS)-cis-3-(Z-2-chloro-3,3,3-trifluoro-1-propenyl)-2,2-dimethylcyclopropanecarboxylate (Compound No. 123). Yield 85% $n_D^{20}$ 1.4618

$^1$H-NMR (CDCl$_3$, internal standard TMS) δ value (ppm) 1.29 (s,6H), 1.95 (d,1H), 2.15 (t,1H), 2.30–2.61 (m,4H), 2.69–2.89 (m,2H), 4.58 (dt,2H), 5.32–5.41 (m,1H), 5.43 (brs,1H), 6.92 (d,1H)

EXAMPLE 21

3-cyclopenten-1-ol (350 mg) was used instead of (RS)-3-ethyl-4-methyl-3-cyclopenten-1-ol used in Example 1 above and the reaction procedures were carried out in the same manner as in Example 1 to afford 928 mg of 3-cyclopenten-1-yl (1RS)-cis-3-(Z-2-chloro-3,3,3-trifluoro-1-propenyl)-2,2-dimethylcyclopropanecarboxylate (Compound No. 126). Yield 78% $n_D^{23}$ 1.4652

$^1$H-NMR (CDCl$_3$, internal standard TMS) δ value (ppm) 1.29 (s,6H), 1.92 (d,1H), 2.12 (t,1H), 2.30–2.47 (m,2H), 2.65–2.82 (m,2H), 5.30–5.41 (m,1H), 5.75 (brs,2H), 6.92 (d,1H)

EXAMPLE 22

(RS)-3-propyl-3-cyclopenten-1-ol (500 mg) and (1RS)-cis-2,2-dimethyl-3-(2,2-dichlorovinyl)cyclopropanecarbonyl chloride (902 mg) were respectively used instead of (RS)-3-ethyl-4-methyl-3-cyclopenten-1-ol and (1RS)-cis- 3-(Z-2-chloro-3,3,3-trifluoro-1-propenyl)-2,2-dimethylcyclopropanecarbonyl chloride used in Example 1 above and the reaction procedures were carried out in the same manner as in Example 1 to afford 1150 mg of (RS)-3-propyl-3-cyclopentenyl (1RS)-cis-3-(Z-2-chloro-3,3,3-trifluoro-1-propenyl)-2,2-dimethylcyclopropanecarboxylate (Compound No. 130). Yield 91% $n_D^{24}$ 1.5038

$^1$H-NMR (CDCl$_3$, internal standard TMS) δ value (ppm) 0.91 (t,3H), 1.22 (s,3H), 1.25 (s,3H), 1.39–1.52 (m,2H), 1.81 (d,1H), 2.01 (dd,1H), 2.09 (t,1H), 2.20–2.47 (m,2H), 2.59–2.83 (m,2H), 5.27–5.39 (m,2H), 6.29 (d,1H)

EXAMPLE 23

(RS)-3-ethyl-3-cyclopenten-1-ol (500 mg) and (1R)-cis-2,2-dimethyl-3-(2,2-dichlorovinyl)cyclopropanecarbonyl chloride (1014 mg) were respectively used instead of (RS)-3-ethyl-4-methyl-3-cyclopenten-1-ol and (1RS)-cis-3-(Z-2-chloro-3,3,3-trifluoro-1-propenyl)-2,2-dimethylcyclopropanecarbonyl chloride used in Example 1 above and the reaction procedures were carried out in the same manner as in Example 1 to afford 1150 mg of (RS)-3-ethyl-3-cyclopentenyl (1R)-cis-2,2-dimethyl-3-(2,2-dichlorovinyl)cyclopropanecarboxylate (Compound No. 132). Yield 80% $n_D^{25}$ 1.5063

$^1$H-NMR (CDCl$_3$, internal standard TMS) δ value (ppm) 1.08 (t,3H), 1.22 (s,3H), 1.25 (s,3H), 1.82 (d,1H), 1.98 (t,1H), 2.01–2.19 (m,1H), 2.20–2.47 (m,2H), 2.58–2.82 (m,2H), 5.22–5.42 (m,2H), 6.26 (dd,1H) Example 24 (RS)-3-bromo-3-cyclopenten-1-ol (100 mg) was used instead of (RS)-3-ethyl-4-methyl-3-cyclopenten-1-ol used in Example 1 above and the reaction procedures were carried out in the same manner as in Example 1 to afford 928 mg of (RS)-3-bromo-3-cyclopenten-1-yl (1RS)-cis-3-(Z-2-chloro-3,3,3-trifluoro-1-propenyl)-2,2-dimethylcyclopropanecarboxylate (Compound No. 133). Yield 83% $n_D^{25}$ 1.4868

$^1$H-NMR (CDCl$_3$, internal standard TMS) δ value (ppm) 1.29 (s,3H), 1.35 (s,3H), 1.93 (d,1H), 2.18 (t,1H), 2.30–2.48 (m,1H), 2.50–2.69 (m,1H), 2.97–3.12 (m,1H), 2.69–2.88 (m,1H), 5.28–5.39 (m,1H), 5.82 (brs,1H), 6.88 (d,1H)

EXAMPLE 25

(RS)-3-propyl-3-cyclopenten-1-ol (500 mg) was used instead of (RS)-3,4-dimethyl-3-cyclopenten-1-ol used in Example 7 above and the reaction procedures were carried out in the same manner as in Example 7 to afford 1180 mg of (RS)-3-propyl-3-cyclopenten-1-yl (1R)-trans-3-(Z-2-chloro-3,3,3-trifluoro-1-propenyl)-2,2-dimethylcyclopropanecarboxylate (Compound No. 135). Yield 85% $n_D^{22}$ 1.4636

$^1$H-NMR (CDCl$_3$, internal standard TMS) δ value (ppm) 0.91 (t,3H), 1.21 (s,3H), 1.32 (s,3H), 1.37–1.52 (m,2H), 1.73 (d,1H), 2.02 (t,2H), 2.19–2.45 (m,3H), 2.61–2.82 (m,2H), 5.26–5.41 (m,2H), 6.12 (d,1H)

Some examples of the compounds of this invention are shown in Table 1 together with the compound number, the compound represented by the formula (I) being indicated by the definition of respective substituents. The groups $Q_1$–$Q_{16}$ represented by $R_3$ in Table 1 respectively correspond to those described in the Annex to Table 1.

Annex to Table 1

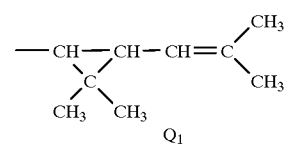

$Q_1$

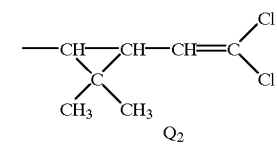

$Q_2$

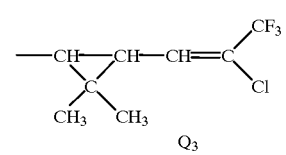

$Q_3$

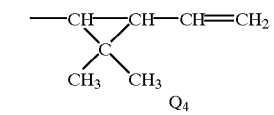

$Q_4$

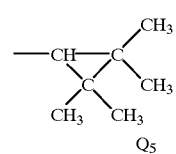

$Q_5$

Annex to Table 1

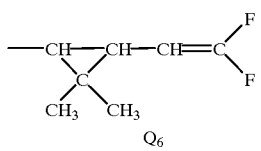
Q₆

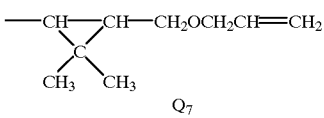
Q₇

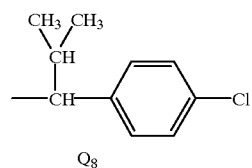
Q₈

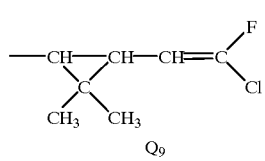
Q₉

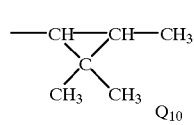
Q₁₀

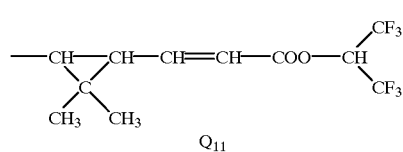
Q₁₁

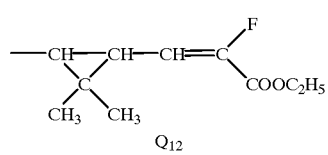
Q₁₂

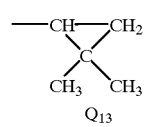
Q₁₃

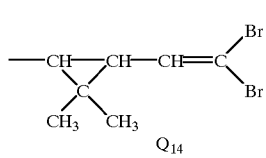
Q₁₄

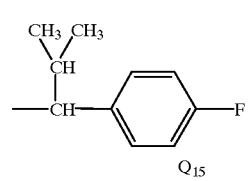
Q₁₅

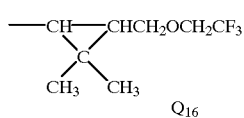
Q₁₆

Table 1

| Compound number | $R_1$ | $R_2$ | Configuration of alcohol moiety | $R_3$ | Configuration of $R_3$ |
|---|---|---|---|---|---|
| 1 | $C_2H_5$ | $CH_3$ | RS | $Q_1$ | 1R-trans |
| 2 | propargyl | $CH_3$ | RS | $Q_2$ | 1R-trans |
| 3 | $CH_3$ | $CH_3$ | RS | $Q_3$ | 1RS-cis(Z) |
| 4 | allyl | $CH_3$ | RS | $Q_5$ | — |
| 5 | propargyl | $CH_3$ | RS | $Q_{10}$ | 1R-cis/trans |
| 6 | propargyl | $CH_3$ | RS | $Q_{13}$ | 1R |
| 7 | propargyl | $CH_3$ | RS | $Q_4$ | 1R-trans |
| 8 | propargyl | $CH_3$ | RS | $Q_{15}$ | S |
| 9 | $C_2H_5$ | H | RS | $Q_1$ | 1R-trans |
| 10 | propargyl | H | RS | $Q_2$ | 1R-trans |
| 11 | $C_2H_5$ | $CH_3$ | RS | $Q_3$ | 1R-cis(Z) |
| 12 | allyl | H | RS | $Q_5$ | — |
| 13 | propargyl | H | RS | $Q_{10}$ | 1R-cis/trans |
| 14 | propargyl | H | RS | $Q_{13}$ | 1R |
| 15 | $CH_3$ | $CH_3$ | RS | $Q_{16}$ | 1R-trans |
| 16 | allyl | $CH_3$ | RS | $Q_8$ | S |
| 17 | propargyl | $CH_3$ | RS | $Q_1$ | 1R-trans |
| 18 | allyl | $CH_3$ | RS | $Q_2$ | 1R-trans |
| 19 | propyl | $CH_3$ | RS | $Q_3$ | 1RS-cis(Z) |
| 20 | propargyl | $CH_3$ | RS | $Q_5$ | — |
| 21 | allyl | $CH_3$ | RS | $Q_{10}$ | 1R-cis/trans |
| 22 | allyl | $CH_3$ | RS | $Q_{13}$ | 1R |
| 23 | propargyl | $CH_3$ | RS | $Q_6$ | 1R-trans |
| 24 | $CH_3$ | $CH_3$ | RS | $Q_9$ | 1R-trans |
| 25 | allyl | $CH_3$ | RS | $Q_7$ | 1R-trans |
| 26 | $C_2H_5$ | $CH_3$ | RS | $Q_1$ | 1R-cis |
| 27 | $C_2H_5$ | H | RS | $Q_1$ | 1R-cis |
| 28 | propargyl | $CH_3$ | RS | $Q_2$ | 1R-cis |
| 29 | allyl | H | RS | $Q_2$ | 1R-trans |
| 30 | $CH_3$ | $CH_3$ | RS | $Q_3$ | 1R-trans(Z) |
| 31 | propargyl | H | RS | $Q_1$ | 1R-trans |
| 32 | $CF_3$ | $CH_3$ | RS | $Q_2$ | 1R-trans |
| 33 | $C_2H_5$ | H | RS | $Q_3$ | 1R-cis(Z) |
| 34 | allyl | $CH_3$ | RS | $Q_3$ | 1R-cis(Z) |
| 35 | allyl | H | RS | $Q_3$ | 1RS-cis(Z) |
| 36 | propargyl | H | RS | $Q_5$ | — |
| 37 | $CF_3$ | $C_2H_5$ | RS | $Q_2$ | 1R-trans |
| 38 | $CF_3$ | H | RS | $Q_2$ | 1R-trans |
| 39 | $CF_2H$ | $CH_3$ | RS | $Q_2$ | 1R-trans |
| 40 | allyl | $CH_3$ | RS | $Q_1$ | 1R-trans |
| 41 | allyl | H | RS | $Q_1$ | 1R-trans |
| 42 | $CF_3$ | $CH_3$ | RS | $Q_1$ | 1R-trans |
| 43 | $CF_3$ | $C_2H_5$ | RS | $Q_1$ | 1R-trans |
| 44 | $CF_2H$ | H | RS | $Q_2$ | 1R-trans |
| 45 | propargyl | $CH_3$ | RS | $Q_3$ | 1RS-cis(Z) |
| 46 | propargyl | H | RS | $Q_3$ | 1RS-cis(Z) |
| 47 | $CF_3$ | $CH_3$ | RS | $Q_3$ | 1RS-cis(Z) |
| 48 | $CF_2H$ | $CH_3$ | RS | $Q_3$ | 1RS-cis(Z) |
| 49 | benzyl | H | RS | $Q_2$ | 1R-trans |
| 50 | $CF_2CH_2$ | $CF_2H$ | RS | $Q_1$ | 1R-trans |
| 51 | $CF_2H$ | $CH_3$ | RS | $Q_1$ | 1R-trans |
| 52 | $CF_2H$ | $C_2H_5$ | RS | $Q_1$ | 1R-trans |
| 53 | F | $CH_3$ | RS | $Q_2$ | 1R-trans |
| 54 | F | H | RS | $Q_2$ | 1R-trans |
| 55 | $CF_3$ | $CH_3$ | RS | $Q_2$ | 1R-cis |
| 56 | $CF_3$ | $C_2H_5$ | RS | $Q_2$ | 1R-cis |
| 57 | F | H | RS | $Q_2$ | 1R-cis |
| 58 | $CF_3$ | H | RS | $Q_3$ | 1RS-cis(Z) |
| 59 | $CF_3CH_2$ | H | RS | $Q_{10}$ | 1R-cis/trans |
| 60 | allyl | $CH_3$ | RS | $Q_9$ | 1R-trans |
| 61 | propargyl | $CH_3$ | RS | $Q_{10}$ | 1R-trans |
| 62 | propargyl | H | RS | $Q_2$ | 1R-cis |
| 63 | allyl | $CH_3$ | RS | $Q_2$ | 1R-cis |

Table 1-continued

| Compound number | $R_1$ | $R_2$ | Configuration of alcohol moiety | $R_3$ | Configuration of $R_3$ |
|---|---|---|---|---|---|
| 64 | allyl | H | RS | $Q_2$ | 1R-cis |
| 65 | $CF_3CH_2$ | $CH_3$ | RS | $Q_3$ | 1RS-cis(Z) |
| 66 | $CF_3CH_2$ | H | RS | $Q_3$ | 1RS-cis(Z) |
| 67 | $CF_3CH_2$ | H | RS | $Q_5$ | — |
| 68 | $CF_3CH_2$ | $CH_3$ | RS | $Q_2$ | 1R-trans |
| 69 | $CF_3CH_2$ | $CH_3$ | RS | $Q_2$ | 1R-cis |
| 70 | $CF_3$ | H | RS | $Q_2$ | 1R-cis |
| 71 | propargyl | $CH_3$ | RS | $Q_1$ | 1R-cis |
| 72 | propargyl | H | RS | $Q_1$ | 1R-cis |
| 73 | allyl | $CH_3$ | RS | $Q_1$ | 1R-cis |
| 74 | $CF_3$ | $CH_3$ | RS | $Q_5$ | — |
| 75 | $CF_2H$ | $CH_3$ | RS | $Q_5$ | — |
| 76 | benzyl | $CH_3$ | RS | $Q_{14}$ | 1R-cis |
| 77 | propargyl | $CH_3$ | RS | $Q_{14}$ | 1R-cis |
| 78 | $CF_3$ | $CH_3$ | RS | $Q_{10}$ | 1R-cis/trans |
| 79 | allyl | H | RS | $Q_1$ | 1R-cis |
| 80 | $CF_3$ | $CH_3$ | RS | $Q_1$ | 1R-cis |
| 81 | $C_2H_5$ | $CH_3$ | RS | $Q_3$ | 1R-trans(Z) |
| 82 | propyl | $CH_3$ | RS | $Q_3$ | 1R-trans(Z) |
| 83 | $C_2H_5$ | H | RS | $Q_3$ | 1R-trans(Z) |
| 84 | $CF_3$ | $CH_3$ | RS | $Q_3$ | 1R-trans(Z) |
| 85 | $CF_2H$ | $CH_3$ | RS | $Q_3$ | 1R-trans(Z) |
| 86 | $CF_3$ | H | RS | $Q_3$ | 1R-trans(Z) |
| 87 | $CF_2H$ | H | RS | $Q_3$ | 1R-trans(Z) |
| 88 | $CF_2H$ | H | RS | $Q_3$ | 1RS-cis(Z) |
| 89 | $CF_2H$ | $CH_3$ | RS | $Q_2$ | 1R-cis |
| 90 | F | $CH_3$ | RS | $Q_2$ | 1R-cis |
| 91 | benzyl | H | RS | $Q_2$ | 1R-cis |
| 92 | propargyl | $CH_3$ | RS | $Q_{11}$ | 1R-trans |
| 93 | propargyl | $CH_3$ | RS | $Q_{12}$ | 1R-trans |
| 94 | $CF_2H$ | $CH_3$ | RS | $Q_{10}$ | 1R-cis/trans |
| 95 | benzyl | $CH_3$ | RS | $Q_5$ | — |
| 96 | allyl | $CH_3$ | RS | $Q_3$ | 1R-trans |
| 97 | propargyl | $CH_3$ | RS | $Q_3$ | 1R-trans |
| 98 | propargyl | H | RS | $Q_3$ | 1R-trans |
| 99 | allyl | H | RS | $Q_3$ | 1R-trans |
| 100 | $CF_2H$ | $CH_3$ | RS | $Q_1$ | 1R-cis |
| 101 | $CF_2H$ | $C_2H_5$ | RS | $Q_1$ | 1R-cis |
| 102 | $CF_3CH_2$ | $CH_3$ | RS | $Q_3$ | 1R-trans(Z) |
| 103 | $CF_3CH_2$ | H | RS | $Q_3$ | 1R-trans(Z) |
| 104 | benzyl | $CH_3$ | RS | $Q_7$ | 1R-trans |
| 105 | benzyl | $CH_3$ | RS | $Q_{11}$ | 1R-trans |
| 106 | $CH_3$ | $CH_3$ | RS | $Q_2$ | 1R-trans |
| 107 | $CH_3$ | $CH_3$ | RS | $Q_1$ | 1R-cis |
| 108 | $CH_3$ | $CH_3$ | RS | $Q_3$ | 1RS-trans |
| 109 | $C_2H_5$ | H | RS | $Q_2$ | 1R-trans |
| 110 | $CH_3$ | $CH_3$ | RS | $Q_1$ | 1R-trans |
| 111 | allyl | $CH_3$ | S | $Q_3$ | 1RS-cis(Z) |
| 112 | $CH_2Cl$ | H | RS | $Q_3$ | 1RS-cis(Z) |
| 113 | a) | H | RS | $Q_3$ | 1RS-cis(Z) |
| 114 | b) | H | RS | $Q_3$ | 1RS-cis(Z) |
| 115 | c) | H | RS | $Q_3$ | 1RS-cis(Z) |
| 116 | benzyl | H | RS | $Q_3$ | 1RS-cis(Z) |
| 117 | allyl | H | RS | $Q_5$ | — |
| 118 | ethyl | H | RS | $Q_3$ | 1RS-cis(Z) |
| 119 | $CH_3$ | H | RS | $Q_3$ | 1RS-cis(Z) |
| 120 | ethyl | H | RS | $Q_3$ | 1RS-trans |
| 121 | propyl | H | RS | $Q_2$ | 1R-trans |
| 122 | propyl | H | RS | $Q_3$ | 1RS-cis(Z) |
| 123 | 2-fluoro-ethyl | H | RS | $Q_3$ | 1RS-cis(Z) |
| 124 | 2-fluoro-ethyl | H | RS | $Q_2$ | 1R-trans |
| 125 | isopropyl | H | RS | $Q_3$ | 1RS-cis(Z) |
| 126 | H | H | RS | $Q_3$ | 1RS-cis(Z) |
| 127 | allyl | H | RS | $Q_2$ | #1RS-cis |
| 128 | propyl | H | RS | $Q_3$ | 1RS-c/t (=1/3) |
| 129 | allyl | H | RS | $Q_3$ | 1RS-c/t (=1/3) |
| 130 | propyl | H | RS | $Q_2$ | 1RS-cis |
| 131 | ethyl | H | RS | $Q_2$ | 1RS-cis |
| 132 | ethyl | H | RS | $Q_2$ | 1R-cis |
| 133 | Br | H | RS | $Q_3$ | 1RS-cis |
| 134 | propyl | H | RS | $Q_2$ | 1RS-c/t (=44/56) |
| 135 | propyl | H | RS | $Q_3$ | 1R-trans(Z) |
| 136 | ethyl | H | RS | $Q_1$ | 1R-trans |
| 137 | $CH_3$ | H | RS | $Q_2$ | 1R-trans |
| 138 | propyl | H | RS | $Q_1$ | 1R-trans |
| 139 | 2-fluoro-ethyl | H | RS | $Q_1$ | 1R-trans |
| 140 | isopropyl | H | RS | $Q_2$ | 1R-trans |
| 141 | isopropyl | H | RS | $Q_1$ | 1R-trans |
| 142 | propargyl | H | RS | $Q_5$ | 1R-trans |
| 143 | Cl | H | RS | $Q_3$ | 1RS-cis(Z) |
| 144 | propargyl | H | S | $Q_3$ | 1RS-cis(Z) |
| 145 | propyl | H | S | $Q_3$ | 1RS-cis(Z) |

Note:
a) 4-fluorobenzyl
b) cyclopentylmethyl
c) 1-methyl-2-propenyl

The physical property (refractive index) of some examples of the ester compound of this invention is shown below. The respective ester compounds are indicated by the compound numbers shown in Table 1, respectively.

| Compound number | Physical property |
|---|---|
| 1 | $n_D^{27}$ 1.4843 |
| 3 | $n_D^{25}$ 1.4620 |
| 10 | $n_D^{23}$ 1.5192 |
| 11 | $n_D^{27}$ 1.4645 |
| 18 | $n_D^{24}$ 1.5112 |
| 29 | $n_D^{25}$ 1.5100 |
| 30 | $n_D^{23}$ 1.4651 |
| 34 | $n_D^{24}$ 1.4721 |
| 35 | $n_D^{25}$ 1.4713 |
| 40 | $n_D^{25}$ 1.4891 |
| 41 | $n_D^{27}$ 1.4895 |
| 46 | $n_D^{23}$ 1.4779 |
| 49 | $n_D^{25}$ 1.5414 |
| 106 | $n_D^{25}$ 1.5041 |
| 107 | $n_D^{23}$ 1.4897 |
| 108 | $n_D^{23}$ 1.4649 |
| 109 | $n_D^{27}$ 1.4843 |
| 110 | $n_D^{23}$ 1.4856 |
| 116 | $n_D^{25}$ 1.5039 |
| 118 | $n_D^{21}$ 1.4629 |
| 119 | $n_D^{21}$ 1.4629 |
| 120 | $n_D^{21}$ 1.4651 |
| 121 | $n_D^{19}$ 1.5030 |
| 122 | $n_D^{23}$ 1.4592 |
| 123 | $n_D^{20}$ 1.4618 |
| 124 | $n_D^{23}$ 1.4951 |
| 125 | $n_D^{21}$ 1.4592 |
| 126 | $n_D^{23}$ 1.4652 |
| 127 | $n_D^{21}$ 1.5179 |
| 128 | $n_D^{20}$ 1.4640 |
| 129 | $n_D^{20}$ 1.4731 |
| 130 | $n_D^{24}$ 1.5038 |
| 131 | $n_D^{25}$ 1.5063 |
| 132 | $n_D^{25}$ 1.5053 |
| 133 | $n_D^{25}$ 1.4868 |
| 134 | $n_D^{22}$ 1.5035 |
| 135 | $n_D^{22}$ 1.4636 |
| 136 | $n_D^{21}$ 1.4845 |
| 137 | $n_D^{21}$ 1.4998 |
| 138 | $n_D^{23}$ 1.4801 |
| 139 | $n_D^{25}$ 1.4789 |
| 140 | $n_D^{21}$ 1.5015 |
| 141 | $n_D^{21}$ 1.4809 |

Then, some examples of the preparation of the alcohol compound represented by the formula (II)' are described below.

Intermediate preperation example 1 (preparation example according to schemes (d) and (a))

(1) To a solution mixture of 8.8 g of (RS)-3-allyl-4-oxo-2-cyclopenten-1-ol, 100 ml of N,N-dimethylformamide and 4.75 g of imidazole was added t-butyldimethylsilyl chloride under ice-cooling, and the resulting mixture was stirred under ice-cooling for 8 hours. Then the reaction liquid was poured into ice-cooled 5% aqueous solution of citric acid and extracted two times with diethyl ether. The combined ether layer was washed successively with saturated aqueous sodium bicarbonate solution and saturated aqueous sodium chloride solution, then dried over anhydrous magnesium sulfate, and the solvent was distilled off under reduced pressure. The residue thus obtained was subjected to silica gel column chromatography to obtain 13.1 g of (RS)-3-allyl-4-oxo-2-cyclopenten-1-yl (t-butyldimethylsilyl) ether. Yield 81%

$^1$H-NMR (CDCl$_3$, internal standard TMS) δ value (ppm) : 0.12 (s,6H), 0.92 (s,9H), 2.28 (dd,1H), 2.79 (dd,1H), 2.93 (d,2H), 4.88–4.93 (m,1H), 5.08–5.20 (m,2H), 5.79–5.92 (m,1H), 7.05–7.10 (m,1H)

(2) To a solution mixture of 5 g of (RS)-3-allyl-4-oxo-2-cyclopenten-1-yl (t-butyldimethylsilyl) ether and 50 ml of tetrahydrofuran was added under nitrogen stream 23.7 ml of 1.07 M diethyl ether solution of methyllithium at −78° C. and the resulting mixture was stirred at the same temperature for 2 hours. Then, the reaction liquid was poured into ice-cooled 5% aqueous solution of citric acid and extracted two times with diethyl ether. The combined ether layer was washed successively with saturated aqueous sodium bicarbonate solution and saturated aqueous sodium chloride solution, then dried over anhydrous magnesium sulfate, and the solvent was distilled off under reduced pressure. The residue thus obtained was subjected to silica gel column chromatography to obtain 4.7 g of (1RS,4RS)-3-allyl-4-methyl-4-hydroxy-2-cyclopenten-1-yl (t-butyldimethylsilyl) ether. Yield 84%

(3) To a solution mixture of 4.7 g of (1RS,4RS)-3-allyl-4-methyl-4-hydroxy-2-cyclopenten-1-yl (t-butyldimethylsilyl) ether, 6.8 g of N,N-diisopropylethylamine and 50 ml of chloroform was added 2.66 ml of chloromethyl methyl ether under ice-cooling and the resulting mixture was allowed to react at room temperature for 8 hours. Then the reaction liquid was poured into ice-cooled 5% aqueous solution of citric acid and extracted two times with diethyl ether. The combined ether layer was washed successively with saturated aqueous sodium bicarbonate solution and saturated aqueous sodium chloride solution, then dried over anhydrous magnesium sulfate, and the solvent was distilled off under reduced pressure. The residue thus obtained was subjected to silica gel column chromatography to obtain 4.5 g of (1RS,4RS)-3-allyl-4-methyl-4-methoxymethoxy-2-cyclopenten-1-yl (t-butyldimethylsilyl) ether. Yield 82%

$^1$H-NMR (CDCl$_3$, internal standard TMS) δ value (ppm) : 0.08 (s,6H), 0.91 (s,9H), 1.31 (s,3H), 2.08 (dd,1H), 2.35 (dd,1H), 2.68–2.92 (m,2H), 3.38 (s,3H), 4.58–4.72 (m,3H), 5.02–5.16 (m,2H), 5.49–5.51 (m,1H), 5.81–5.98 (m,1H)

(4) To a solution mixture of 4.5 g of (1RS,4RS)-3-allyl-4-methyl-4-methoxymethoxy-2-cyclopenten-1-yl (t-butyldimethylsilyl) ether and 50 ml of dichloromethane was added under nitrogen stream 3 ml of triethylsilane by drops at −78° C., and the resulting mixture was stirred for 15 minutes. Thereafter, under the same conditions, 17.5 ml of 0.93 M hexane solution of ethylaluminum dichloride was added by drops and the resulting mixture was brought up to −10° C. over 1 hour. Then the reaction liquid was poured into ice-cooled 5% aqueous solution of citric acid and extracted with diethyl ether. The ether layer was washed successively with saturated aqueous sodium bicarbonate solution and saturated aqueous sodium chloride solution, then dried over anhydrous magnesium sulfate and the solvent was distilled off under reduced pressure. The residue thus obtained was subjected to silica gel column chromatography to obtain 2 g of (RS)-3-allyl-4-methyl-3-cyclopenten-1-yl (t-butyldimethylsilyl) ether. Yield 55%

$^1$H-NMR (CDCL$_3$, internal standard TMS) δ value (ppm) : 0.09 (s,6H), 0.90 (s,9H), 1.61 (s,3H), 2.19–2.35 (m,2H), 2.47–2.61 (m,2H), 2.72–2.82 (m,2H), 4.31–4.49 (m,1H), 4.91–5.09 (m,2H), 5.62–5.82 (m,1H)

(5) To a solution of 2 g of (RS)-3-allyl-4-methyl-3-cyclopenten-1-yl (t-butyldimethylsilyl) ether in 20 g of tetrahydrofuran was added under ice-cooling 16 ml of 1 M tetrahydrofuran solution of tetrabutylammonium fluoride, and the resulting mixture was stirred at room temperature for 6 hours. Then the reaction liquid was poured into ice water and extracted with diethyl ether. The ether layer was washed with saturated aqueous sodium chloride solution, then dried over anhydrous magnesium sulfate and the solvent was distilled off under reduced pressure. The oily substance thus obtained was subjected to silica gel column chromatography to obtain 0.58 g of (RS)-3-allyl-4-methyl-3-cyclopenten-1-ol. Yield 53%

$^1$H-NMR (CDCl$_3$, internal standard TMS) δ value (ppm) : 1.51 (d,1H), 1.69 (s,3H), 2.15–2.32 (m,2H), 2.54–2.78 (m,2H), 2.83 (d,2H), 4.32–4.48 (m,1H), 4.91–5.09 (m,2H), 5.12–5.83 (m,1H)

Intermediate preparation example 2 (preparation example according to schemes (d) and (a))

(1) From 2.3 g of (RS)-3-ethyl-4-oxo-2-cyclopenten-1-ol was obtained by the same procedures as in (1) of the intermediate preparation example 1 (RS)-3-ethyl-4-oxo-2-cyclopenten-1-yl (t-butyldimethylsilyl) ether in an amount of 4.1 g. Yield 93%

$^1$H-NMR (CDCl$_3$, internal standard, TMS) δ value (ppm) : 0.12 (s,6H), 0.92 (s,9H), 2.28 (dd,1H), 2.79 (dd,1H), 2.93 (d,2H), 4.88–5.93 (m,1H), 5.08–5.20 (m,2H), 5.79–5.92 (m,1H), 7.05–7.10 (m,1H)

(2) To a liquid mixture of 2 g of (RS)-3-ethyl-4-oxo-2-cyclopenten-1-yl (t-butyldimethylsilyl) ether and 20 ml of tetrahydrofuran was added under nitrogen stream 10 ml of 1.07 M diethyl ether solution of methyllithium at −78° C. and the resulting mixture was stirred at the same temperature for 2 hours. Then the reaction liquid was poured into ice-cooled 5% aqueous solution of citric acid and extracted two times with diethyl ether. The combined ether layer was washed successively with saturated aqueous sodium bicarbonate solution and saturated aqueous sodium chloride solution, then dried over anhydrous magnesium sulfate, and the solvent was distilled off under reduced pressure. The residue thus obtained was subjected to silica gel column chromatography to obtain 2.1 g of (1RS,4RS)-3-ethyl-4-methyl-4-hydroxy-2-cyclopenten-1-yl (t-butyldimethylsilyl) ether. Yield 98%

(3) To a solution mixture of 2.1 g of (1RS,4RS)-3-ethyl-4-methyl-4-hydroxy-2-cyclopenten-1-yl (t-butyldimethylsilyl) ether, 2.7 g of N,N-diisopropylethylamine and 30 ml of chloroform was added under ice-cooling 1.24 ml of chloromethyl methyl ether, and the resulting mixture was allowed to react at room temperature for 8 hours. Then the reaction liquid was poured into ice-cooled 5% aqueous solution of citric acid and extracted two times with diethyl ether. The combined ether layer was washed successively with saturated aqueous sodium bicarbonate solution and saturated aqueous sodium chloride solution, then dried over anhydrous magnesium sulfate, and the solvent was distilled off under reduced pressure. The residue thus obtained was subjected to silica gel column chromatography to obtain 2.35 g of (1RS,4RS)-3-ethyl-4-methyl-4-methoxymethoxy-2-cyclopenten-1-yl (t-butyldimethylsilyl) ether. Yield 95%

$^1$H-NMR (CDCl$_3$, internal standard TMS) δ value (ppm) : 0.09 (s,6H), 0.91 (s,9H), 1.11 (t,3H), 1.29 (s,3H), 1.88–2.12 (m,3H), 2.31 (dd,1H), 3.38 (s,3H), 4.56–4.62 (m,1H), 4.65 (s,2H), 5.48–5.51 (m,1H)

(4) To a solution mixture of 2.35 g of (1RS,4RS)-3-ethyl-4-methyl-4-methoxymethoxy-2-cyclopenten-1-yl (t-butyldimethylsilyl) ether and 25 ml of dichloromethane was added under nitrogen stream and at −78° C. 1.4 ml of triethylsilane by drops, and the resulting mixture was stirred for 15 minutes. Thereafter, under the same conditions, 8.17 ml of 0.93 M hexane solution of ethylaluminum dichloride was added by drops and the resulting mixture was brought up to −10° C. over 1 hour. Thereafter, the reaction liquid was poured into ice-cooled 5% aqueous solution of citric acid and extracted with diethyl ether. The ether layer was washed successively with saturated aqueous sodium bicarbonate solution and saturated aqueous sodium chloride solution, then dried over anhydrous magnesium sulfate, and the solvent was distilled off under reduced pressure. The residue thus obtained was subjected to silica gel column chromatography to obtain 1 g of (RS)-3-ethyl-4-methyl-3-cyclopenten-1-yl (t-butyldimethylsilyl) ether. Yield 53%

$^1$H-NMR (CDCl$_3$, internal standard TMS) δ value (ppm) : 0.08 (s,6H), 0.89 (s,9H), 0.99 (t,3H), 1.58 (s,3H), 2.05 (q,2H), 2.15–2.31 (m,2H), 2.45–2.63 (m,2H), 4.39–4.50 (m,1H)

(5) From 1.00 g of (RS)-3-ethyl-4-methyl-3-cyclopenten-1-yl (t-butyldimethylsilyl) ether was obtained by the same procedures as in (5) of the intermediate preparation example 1 (RS)-3-ethyl-4-methyl-3-cyclopenten-1-ol in an amount of 0.24 g. Yield 46%

$^1$H-NMR (CDCl$_3$, internal standard TMS) δ value (ppm) : 0.98 (t,3H), 1.52 (d,1H), 1.63 (s,3H), 2.11 (q,2H), 2.19–2.31 (m,2H), 2.60–2.75 (m,2H), 4.32–4.48 (m,1H)

Intermediate preparation example 3 (preparation example according to schemes (d) and (a))

(1) To a solution mixture of 3.5 g of (RS)-4-oxo-2-cyclopenten-1-yl (t-butyldimethylsilyl) ether obtained according to the method described in Org. Syn., Vol 73, p. 36 and 35 ml of tetrahydrofuran was added under nitrogen stream and at 0° C. 11 ml of 2.0 M diethyl ether solution of allylmagnesium chloride and the resulting mixture was stirred at the same temperature for 1 hour. Then the reaction liquid was poured into ice-cooled saturated aqueous ammonium chloride solution and extracted two times with diethyl ether. The combined ether layer was washed with saturated aqueous sodium chloride solution, then dried over anhydrous magnesium sulfate, and the solvent was distilled off under reduced pressure. The residue thus obtained was subjected to silica gel column chromatography to obtain 4.1 g of (1RS,4RS)-4-allyl-4-hydroxy-2-cyclopenten-1-yl (t-butyldimethylsilyl) ether. Yield 98%

(2) From 4.50 g of (1RS,4RS)-4-allyl-4-hydroxy-2-cyclopenten-1-yl (t-butyldimethylsilyl) ether was obtained by the same procedures as in (3) of the intermediate preparation example 1 (1RS,4RS)-4-allyl-4-methoxymethyl-2-cyclopenten-1-yl (t-butyldimethylsilyl) ether in an amount of 4.88 g. Yield 92%

$^1$H-NMR (CDCl$_3$, internal standard TMS) δ value (ppm) : 0.03 (s,6H), 0.89 (s,9H), 1.68–1.88 (m,1H), 2.27–2.54 (m,3H), 3.38 (s,3H), 1.52–4.68 (m,1H), 4.72 (dd,2H), 5.01–5.14 (m,2H), 5.68–5.95 (m,3H)

(3) From 4.88 g of (1RS,4RS)-4-allyl-4-methoxymethoxy-2-cyclopenten-1-yl (t-butyldimethylsilyl) ether was obtained by the same procedures as in (4) of the intermediate preparation example 1 (RS)-3-allyl-3-cyclopenten-1-yl (t-butyldimethylsilyl) ether in an amount of 1.64 g. Yield 42%

$^1$H-NMR (CDCl$_3$, internal standard TMS) δ value (ppm) : 0.06 (s,6H), 0.89 (s,9H), 2.11–2.39 (m,2H), 2.42–2.70 (m,2H), 2.82 (d,1H), 4.48–4.60 (m,1H), 4.91–5.14 (m,2H), 5.28–5.32 (m,1H), 5.71–5.92 (m,1H)

(4) From 1.64 g of (RS)-3-allyl-3-cyclopenten-1-yl (t-butyldimethylsilyl) ether was obtained by the same procedures as in (5) of the intermediate preparation example 1 (RS)-3-allyl-3-cyclopenten-1-ol in an amount of 0.30 g. Yield 18%

$^1$H-NMR (CDCl$_3$, internal standard TMS) δ value (ppm) : 1.58 (brs,1H), 2.15–2.35 (m,2H), 2.52–2.78 (m,2H), 2.86 (d,2H), 4.41–4.58 (M,1H), 4.98–5.14(m,2H), 5.29–5.40 (m,1H), 5.73–5.94 (m,1H)

Intermediate preparation example 4 (preparation example according to schemes (d) and (a))

(1) To a solution mixture of 6.5 g of trimethylsilyl-1-propyne and 50 ml of tetrahydrofuran was added under nitrogen stream and at −30° C. 17.4 ml of 1.56 M hexane solution of n-butyllithium and the resulting mixture was stirred at the same temperature for 1 hour. Then, a solution mixture of 10 g of (RS)-4-oxo-2-cyclopenten-1-yl (t-butyldimethylsilyl) ether and 100 ml of tetrahydrofuran was added by drops to the reaction solution obtained above, and the resulting mixture was stirred for further one hour. The reaction liquid thus obtained was after-treated and purified in the same manner as in (2) of the intermediate preparation example 1 to obtain 8.9 g of (1RS,4RS)-4-hydroxy-4-(3-trimethylsilyl-2-propynyl)-2-cyclopenten-1-yl (t-butyldimethylsilyl) ether. Yield 59%

(2) From 8.9 g of (1RS,4RS)-4-hydroxy-4-(3-trimethylsilyl-2-propynyl)-2-cyclopenten-1-yl (t-butyldimethylsilyl) ether was obtained by the same procedures as in (3) of the intermediate preparation example 1 (1RS,4RS)-4-methoxymethoxy-4-(3-trimethylsilyl-2-propynyl)-2-cyclopenten-1-yl (t-butyldimethylsilyl) ether in an amount of 6.6 g. Yield 65%

(3) From 6.6 g of (1RS,4RS)-4-methoxymethoxy-4-(3-trimethylsilyl-2-propynyl)-2-cyclopenten-1-yl (t-butyldimethylsilyl) ether was obtained by the same procedures as in (4) of the intermediate preparation example 1 (RS)-3-(3-trimethylsilyl-2-propynyl)-3-cyclopenten-1-yl (t-butyldimethylsilyl) ether in an amount of 0.85 g. Yield 15%

(4) By using 0.85 g of (RS)-3-(3-trimethylsilyl-2-propynyl)-3-cyclopenten-1-yl (t-butyldimethylsilyl) ether and 8.5 ml of 1 M tetrahydrofuran solution of tetrabutylammonium fluoride and by the same procedures as in (5) of the intermediate preparation example 1, there was obtained 128 mg of (RS)-3-propargyl-3-cyclopenten-1-ol. Yield 37%

$^1$H-NMR (CDCl$_3$, internal standard TMS) δ value (ppm) : 1.61 (brs,1H), 2.09 (t,1H), 2.18–2.42 (m,2H), 2.62–2.79 (m,2H), 2.98 (brs,1H), 4.57 (brs,1H), 5.61 (brs,1H)

Intermediate preparation example 5 (preparation example according to schemes (e) and (a))

(1) By using 2.2 g of 3-cyclopentenol prepared according to the method described in J. Org. Chem., 25, 26–29 (1960) and 9.2 g of t-butyldiphenylsilyl chloride and by the same procedures as in (1) of the intermediate preparation example 1, there was obtained 8.15 g of 3-cyclopenten-1-yl (t-butyldiphenylsilyl) ether. Yield 97%

(2) To a solution mixture of 4 g of 3-cyclopenten-1-yl (t-butyldiphenylsilyl) ether and 30 ml of chloroform was added under ice-cooling 2.1 g of bromine, and the resulting mixture was stirred at the same temperature for 1 hour. Then the reaction liquid was poured into 10% aqueous sodium sulfite solution and extracted two times with diethyl ether. The ether layers were combined and the solvent was distilled off under reduced pressure to obtain 5.41 g of 3,4-dibromocyclopenten-1-yl (t-butyldiphenylsilyl) ether. Yield 93%

(3) To a solution mixture of 4.5 g of 3,4-dibromocyclopenten-1-yl (t-butyldiphenylsilyl) ether and 50 ml of tetrahydrofuran were added at room temperature 910 mg of sodium amide and 3.25 g of t-butoxysodium, and the resulting mixture was stirred for 3.5 hours. The reaction liquid obtained was after-treated and purified in the same manner as in (1) of the intermediate preparation example 1 to obtain 2.53 g of (RS)-3-bromo-3-cyclopenten-1-yl (t-butyldimethylsilyl) ether. Yield 68%

Intermediate preparation example 6 (preparation example according to schemes (f) and (a))

(1) To a solution mixture of 5 g of (RS)-4-oxo-2-cyclopenten-1-yl (t-butyldimethylsilyl) ether prepared according to the method described in Org. Syn., Vol. 73, p. 36 and 75 ml of tetrahydrofuran was added under nitrogen stream and at −78° C. 23.5 ml of lithium tri-sec-butyl borohydride and the resulting mixture was stirred for 1.5 hours. Then 8.41 g of N-phenyltrifluoromethanesulfonimide was added thereto and stirred for 18 hours. The reaction liquid obtained was after-treated and purified in the same manner as in (1) of the intermediate preparation example 1 to obtain 5.5 g of 3-trifluoromethanesulfonyloxy-3-cyclopenten-1-yl (t-butyldimethylsilyl) ether. Yield 68%

(2) To an ether solution of dimethylcopper-lithium obtained by using 8.41 ml of 1.4 M diethyl ether solution of methyllithium, 1.16 g of copper (I) iodide and 15 ml of diethyl ether was added at −30° C. under nitrogen stream 700 mg of 3-trifluoromethanesulfonyloxy-3-cyclopenten-1-yl (t-butyldimethylsilyl) ether and the resulting mixture was stirred for 1 hour. The reaction liquid obtained was after-treated and purified in the same manner as in (1) of the intermediate preparation example 1 to obtain 176 mg of 3-methyl-3-cyclopenten-1-yl (t-butyldimethylsilyl) ether. Yield 41%

$^1$H-NMR (CDCl$_3$, internal standard TMS) δ value (ppm) : 0.08 (s,6H), 3.91 (s,9H), 1.70 (s,3H), 2.11–2.32 (m,2H), 2.41–2.67 (m,2H), 4.48–4.59 (m,1H), 5.18–5.28 (m,1H)

(3) From 176 mg of 3-methyl-3-cyclopenten-1-yl (t-butyldimethylsilyl) ether was obtained by the same procedures as shown in (5) of the intermediate preparation example 1 (RS)-3-methyl-3-cyclopenten-1-ol in an amount of 15 mg. Yield 18%

(4) From 2.53 g of (RS)-3-bromo-3-cyclopenten-1-yl (t-butyldimethylsilyl) ether was obtained by the same procedures as shown in (5) of the intermediate preparation example 1 (RS)-3-bromo-3-cyclopenten-1-ol in an amount of 570 mg. Yield 56%

$^1$H-NMR (CDCl$_3$, internal standard TMS) δ value (ppm) : 1.71 (d,1H), 2.21–2.38 (m,1H), 2.50–2.61 (m,1H), 2.62–2.75 (m,1H), 2.89–3.01 (m,1H), 4.45–4.61 (m,1H), 5.83 (t,1H)

Intermediate preparation example 7 (preparation example according to scheme (b))

(1) To a solution mixture of 33.3 g of 2,2,6,6-tetramethylpiperidine and 235 ml of anhydrous diethyl ether was added under nitrogen stream and at −10° C. to −15° C. 129 ml of 1.68 M hexane solution of n-butyllithium by drops over a period of 15 minutes, and the resulting mixture was stirred for 15 minutes. The reaction liquid thus obtained was added by drops under nitrogen stream and at −10° C. to −15° C. to a solution mixture of 48.4 g of 2,3-dimethyl-1,3-butadiene, 30.4 g of β-chloroethyl chloromethyl ether and 165 ml of anhydrous diethyl ether over a period of 1 hour and stirred at room temperature for 4 hours. The resulting reaction liquid was poured into ice-cooled 5% aqueous solution of citric acid and extracted with diethyl ether. The ether layer was successively washed two times with ice-cooled 5% aqueous solution of citric acid, one time with saturated aqueous sodium bicarbonate solution and one time with saturated aqueous sodium chloride solution, then dried over anhydrous magnesium sulfate and the solvent was distilled off under reduced pressure.

(2) The oily substance, 26 g, obtained above was dissolved in 50 ml of tetrahydrofuran. The resulting solution was added by drops under nitrogen stream and at room temperature to a solution mixture of 53.4 g of hexamethylphosphoric triamide, 442.8 ml of 1.68 M hexane solution of n-butyllithium and 100 ml of tetrahydrofuran was stirred for 5 hours. The reaction liquid thus obtained was poured into ice-cooled 5% aqueous solution of citric acid and extracted with diethyl ether. The ether layer was successively washed two times with ice-cooled 5% aqueous solution of citric acid, one time with saturated aqueous sodium bicarbonate solution and one time with saturated aqueous sodium chloride solution, then dried over anhydrous magnesium sulfate and the solvent was distilled off under reduced pressure. The oily substance obtained was subjected to silica gel column chromatography (developing solvent : hexane/ethyl acetate=1/1) to obtain 1.5 g of (RS)-3,4-dimethyl-3-cyclopenten-1-ol. Yield 6.2%

$^1$H-NMR (CDCl$_3$, internal standard TMS) δ value (ppm) : 1.49–1.60 (m,1H), 1.63 (s,6H), 2.11–2.28 (m,2H), 2.55–2.77 (m,2H), 4.32–4.49 (m,1H)

Intermediate preparation example 8 (preparation example according to scheme (c))

To 25 ml of 2 M tetrahydrofuran solution of sodium cyclopentadienylide was added under ice-cooling and under nitrogen stream 6.3 g of 1-bromo-2-fluoroethane and stirred for 2 hours. The resulting reaction liquid was filtered with cerite, and the filtrate was added under ice-cooling and under nitrogen stream to a tetrahydrofuran solution of disiamylborane prepared by using 75 ml of 1 M borane-tetrahydrofuran complex and 18.5 ml of 2-methyl-2-butene and the resulting mixture was stirred for 8 hours. Then 3 N aqueous sodium hydroxide solution and 30% aqueous hydrogen peroxide were successively added under ice-cooling to the reaction liquid obtained above, and the resulting mixture was stirred for 1 hour. The reaction liquid thus obtained was extracted two times with diethyl ether. The combined ether layer was washed with saturated aqueous sodium chloride solution, then dried over anhydrous magnesium sulfate, and the solvent was distilled off under reduced pressure. The residue obtained was subjected to silica gel column chromatography to obtain 1.1 g of (RS)-3-(2-fluoroethyl)-3-cyclopenten-1-ol. Yield 16%

$^1$H-NMR (CDCl$_3$, internal standard TMS) δ value (ppm) : 1.62 (d,1H), 2.15–2.79 (m,6H), 4.57 (dt,2H), 4.41–4.61 (m,1H), 5.48 (brs,1H)

Now, some formulation examples are shown below, wherein "part" means "part by weight" and the compounds of this invention are indicated by the compound numbers shown in Table 1.

FORMULATION EXAMPLE 1

Emulsifiable Concentrate

Each 20 parts of the compounds 1–145 of this invention is dissolved in 65 parts of xylene, then 15 parts of an emulsifier, Sorpol 3005X (a registered trade mark, Toho Chemical Co., Ltd.) is added thereto and mixed thoroughly with stirring to obtain a 20% emulsifiable concentrate of each compound.

FORMULATION EXAMPLE 2

Wettable Powders

To each 40 parts of the compounds 1–145 of this invention is added 5 parts of Sorpol 3005X (described above) and mixed well. Then, 32 parts of Carplex #80 (synthetic hydrated silicon oxide fine powder, a registered trade mark of Shionogi & Co., Ltd.) and 23 parts of 300-mesh diatomaceous earth are added thereto and mixed with stirring in a juice mixer to obtain 40% wettable powders of each compound.

FORMULATION EXAMPLE 3

Granules

Each 1.5 parts of the compounds 1–145 of this invention and 98.5 parts of AGSORBLVM-MS 24/48 (calcined montmorillonite, granular carrier of 24–48 mesh particle size, mfd. by OIL DRI Corp.) are mixed thoroughly to obtain 1.5% granules of each compound.

FORMULATION EXAMPLE 4

Microcapsules

Each 10 parts of the compounds 1–145 of this invention, 10 parts of phenylxylylethane and 0.5 part of Sumijule L-75 (a trade name, tolylene diisocyanate, mfd. by Sumitomo-Bayer Urethane Co., Ltd.) are mixed and the mixture is added to 20 parts of 10% aqueous solution of gum arabic. The resulting mixture is stirred with a Homomixer to obtain an emulsion with an average particle diameter of 20 $\mu$m. Then 2 parts of ethylene glycol is added to the emulsion, and the mixture is allowed to react in a warm bath at 60° C. for 24 hours to obtain a microcapsule slurry.

Separately, 0.2 part of xanthan gum and 1.0 part of Veegum R (a trade name, aluminum magnesium silicate, mfd. by Sanyo Chemical Industries, Ltd.) are dispersed in 56.3 parts of deionized water to obtain a thickener solution.

Then 42.5 parts of the microcapsule slurry and 57.5 parts of the thickener solution are mixed to obtain 10% microcapsules of each compound.

FORMULATION EXAMPLE 5

Flowable Formulation

Each 10 parts of the compounds 1–145 of this invention and 10 parts of phenylxylylethane are mixed, and the mixture is added to 20 parts of 10% aqueous solution of polyethylene glycol and the resulting mixture is stirred with a Homomixer to obtain an emulsion with an average particle diameter of 3 $\mu$m.

Separately, 0.2 part of xanthan gum, 1.0 part of Veegum R (a trade name, aluminum magnesium silicate, mfd. by Sanyo Chemical Industries, Ltd.) are dispersed in 58.8 parts of deionized water to obtain a thickener solution.

Then, 40 parts of the emulsion and 60 parts of the thickener solution are mixed to obtain a 10% flowable formulation of each compound.

FORMULATION EXAMPLE 6

Dusts

Each 5 parts of the compounds 1–145 of this invention, 3 parts of Carplex #80 (described above), 0.3 part of PAP and 91.7 parts of 300-mesh talc are mixed by stirring in a juice mixer to obtain 5% dusts of each compound.

FORMULATION EXAMPLE 7

Oil Formulation

Each 0.1 part of the compounds 1–145 of this invention is dissolved in 5 parts of dichloromethane, and the resulting solution is mixed into 94.9 parts of deodorized kerosene to obtain a 0.1% oil formulation of each compound.

FORMULATION EXAMPLE 8

Oil-base Aerosol

Each 1 part of the compounds 1–145 of this invention, 5 parts of dichloromethane and 34 parts of deodorized kerosene are mixed to form a solution. The solution is filled in an aerosol container, a valve member is attached to the container, and then 60 parts of a propellant (liquefied petroleum gas) is filled into the container through the valve member under applied pressure to obtain an oil-base aerosol of each compound.

FORMULATION EXAMPLE 9

Water-base Aerosol

Each 0.6 part of the compounds 1–145 of this invention, 5 parts of xylene, 3.4 parts of deodorized kerosene and 1 part of an emulsifier (Atmos 300, a registered trade mark, Atlas Chemical Corp.) are mixed to form a solution. The entire solution and 50 parts of pure water are filled in an aerosol container, a valve member is attached to the container, and 40 parts of a propellant (liquefied petroleum gas) is filled into the container through the valve member under applied pressure to obtain a water-base aerosol of each compound.

FORMULATION EXAMPLE 10

Mosquito Coil

Each 0.3 g of the compounds 1–145 of this invention is dissolved in 20 ml of acetone, and the resulting solution is uniformly mixed by stirring with 99.7 g of a carrier for mosquito coils (a mixture of tabu powder, sake lees powder and wood flour in the ratio of 4:3:3). Then 120 ml of water is added to the mixture obtained above and the resulting mixture is kneaded thoroughly. The kneaded mixture is molded and dried to obtain a mosquito coil of each compound.

FORMULATION EXAMPLE 11

Electrical Mosquito Mat

Each 0.8 g of the compounds 1–145 of this invention and 0.4 g of piperonyl butoxide are dissolved in acetone to prepare a 10 ml solution. With a 0.5 ml portion of the solution obtained above is uniformly impregnated an electrical mat base material (a product obtained by compressing the fibrils of a mixture of cotton linter and pulp into the form of solid plate) of 2.5 cm by 1.5 cm by 0.3 cm thickness to obtain an electrical mosquito mat of each compound.

FORMULATION EXAMPLE 12

Electrical Liquid Mosquito Killer

Each 3 parts of the compounds 1–145 of this invention is dissolved in 97 parts of deodorized kerosene. The solution is put in a poly(vinyl chloride) container, a liquid-absorptive wick (obtained by forming inorganic powder into a solid with the aid of a binder, followed by sintering) is inserted thereto such that the upper part of the wick can be heated with a heater, to obtain an electrical liquid mosquito killer of each compound.

FORMULATION EXAMPLE 13

Heating Smoking Formulation

Each 100 mg of the compounds 1–145 of this invention is dissolved in an appropriate amount of acetone, and with the solution is impregnated a porous ceramic plate of 4.0 cm by 4.0 cm by 1.2 cm thickness to obtain a heating smoking formulation of each compound.

FORMULATION EXAMPLE 14

Normal Temperature Transpiratory Formulation

Each 100 μg of the compounds 1–145 of this invention is dissolved in an appropriate amount of acetone, the resultant solution is uniformly applied onto a filter paper sheet of 2 cm by 2 cm by 0.3 mm thickness and the acetone is air-dried to obtain a normal temperature transpiratory formulation of each compound.

FORMULATION EXAMPLE 15

Mite-proofing Sheet

Each of the compounds 1–145 of this invention is dissolved in acetone, the resultant solution is dropped onto filter paper to impregnate the paper such that the amount of the impregnated compound may be 1 g per square meter of filter paper, and the acetone is air-dried to obtain a mite-proofing sheet of each compound.

Next, the usefulness of the compound of this invention as an active ingredient of pesticidal compositions is demonstrated below by Test Examples.

TEST EXAMPLE 1

Insecticidal Test on German Cockroach

The compound to be tested was diluted with acetone to a predetermined concentration, and the resulting liquid dilution was applied to the abdominal side of the thorax of a German cockroach female adult so as to give the active ingredient in a dose of 10 μg/insect. After 7 days, the numbers of dead and alive insects were examined to calculate the mortality. Separately, a group of insects was treated with acetone containing no active ingredient and was referred to as the untreated group. (10 insects per group, 3 replications).

Resultantly, the compounds 18, 29, 49 and 116 of this invention respectively showed a mortality of 100%. The mortality of the untreated group was 0%.

TEST EXAMPLE 2

Insecticidal Test on Housefly

The compound to be tested was diluted with acetone to a predetermined concentration, and the resulting liquid dilution was applied to the back side of the thorax of a housefly female adult so as to give the active ingredient in a dose of 5 μg/insect. The insects were fed with water and food and were examined for the numbers of alive, moribund and dead insects after 24 hours to calculate the percentage of dead and moribund insects. Separately, a group of insects was treated with acetone containing no active ingredient and was referred to as the untreated group. (10 insects per group, 2 replications)

Resultantly, the compounds 1, 3, 10, 11, 18, 19, 29, 30, 34, 35, 40, 41, 106, 108, 109, 110, 112, 117, 120, 121, 122, 123, 124, 125, 127, 130, 131, 132, 135, 136, 137, 138, 139, 140 and 141 respectively showed a dead and moribund percentage of 100%. The untreated group showed a dead and moribund percentage of 0%.

TEST EXAMPLE 3

Insecticidal Test on Housefly by Means of Normal Temperature Transpiration

Onto an aluminum dish with a bottom diameter of 7 cm was applied by drops 0.64 ml of 0.25% (w/v) acetone dilution of the compound to be tested, and then the acetone was air-dried. Twenty housefly female adults were released into a polyethylene cup 9 cm in diameter and 4.5 cm in height, and a 16-mesh nylon net was provided at the upper part of the cup for preventing the insects from directly contacting with the insecticide-treated surface of the aluminum dish. The cup was inverted and placed on the aluminum dish. After 120 minutes at 25° C., the cup was removed from the aluminum dish and the insects were fed with water and food. After 24 hours, the numbers of alive, moribund and dead insects were examined to calculate the percentage of moribund and dead insects (2 replications).

Resultantly, the compounds, 1, 3, 10, 18, 19, 29, 30, 34, 35, 40, 41, 46, 106, 108, 109, 110, 112, 117, 118, 119, 120, 121, 122, 123, 124, 125, 136, 137, 138, 139, 140 and 141 of this invention respectively showed a percentage of moribund and dead insects of 100%, the compound 107 showed said percentage of 90%, and the compound 11 showed said percentage of 95%.

TEXT EXAMPLE 4

Insecticidal Test on Pale House Mosquito

Onto an aluminum dish with a bottom diameter of 7 cm was applied by drops 0.64 ml of 0.05% (w/v) acetone dilution of the compound to be tested, and then the acetone was air-dried. The pale house mosquito female adults were released into a polyethylene cup 9 cm in diameter and 4.5 cm in height, and a 16-mesh nylon net was provided at the upper part of the cup for preventing the insects from directly contacting with the insecticide-treated surface of the aluminum dish. The cup was inverted and placed on the aluminum dish. After 120 minutes at 25° C., the cup was removed from the aluminum dish and the insects were fed with water and food. The numbers of dead and alive insects after 24 hours were examined to calculate the mortality (2 replications).

Resultantly, the compounds 3, 10, 11, 29, 30, 34, 35, 40, 41, 46, 109, 118, 119, 120, 121, 122, 123, 124, 125, 136, 137, 138, 139, 140 and 141 of this invention respectively showed a mortality of 100%.

TEST EXAMPLE 5

Insecticidal Test on Webbing Clothes Moth

The compound to be tested was diluted with acetone to a predetermined concentration, and the resulting liquid dilution was applied to the central part of the back of a middle instar larva of webbing clothes moth so as to give the active ingredient in a dose of 3 μg/insect. A wool muslin fabric 2 cm by 2 cm in size was given as the food. After 7 days, the mortality and the degree of damage of the wool muslin fabric by the worms were examined. The criterion for the degree of the damage is as follows.

+++: severe damage
++: substantial damage
+: some damage
±: slight damage
−: no damage Separately, a group of the insects was treated with acetone containing no active ingredient and was referred to as the untreated group. (10 insects per group, 2 replications).

Resultantly, the compounds 3, 10, 11, 18, 29, 30, 34, 35, 40, 41, 46, 106, 107, 108, 109, 112, 118, 120, 121, 122, 123, 124, 125, 127, 128, 129, 130, 131, 132, 133, 134, 135, 136, 137, 138, 139, 140 and 141 of this invention respectively showed a mortality of 100% and a degree of damage by worms of −. In contrast, the untreated group showed a mortality of 0% and a degree of damage by worms of +++.

TEST EXAMPLE 6

Insecticidal Test on Webbing Clothes Moth by Means of Normal Temperature Transpiration A wool muslin fabric 2 cm by 2 cm in size and 10 middle instar larvae of webbing clothes moth were placed on the bottom of a polyethylene cup (bottom part diameter 10 cm, opening part diameter 12.5 cm, height 9.5 cm, volume 950 cm³). Then, the cup was tightly sealed with a cap having a normal temperature transpiratory formulation prepared according to Formulation Example 14 so that the formulation was hung from the cap in the interior of the cup. After standing at 25° C. for 1 week, the cup was opened and the numbers of alive, moribund and dead insects were examined to determine the percentage of moribund and dead insects.

Resultantly, the compounds 3, 11, 18, 19, 29, 30, 34, 35, 40, 41, 46, 106, 108, 109, 118, 119, 120, 121, 122, 123, 124, 125, 127, 128, 129, 130, 131, 132, 133, 134, 135, 136, 137, 138, 139, 140 and 141 of this invention respectively showed a percentage of moribund and dead insects of 100% and the compound 1 showed said percentage of 80%.

TEST EXAMPLE 7

Controlling Test on *Dermatophagoides farinae*

The mite-proofing sheet obtained according to Formulation Example 15 was cut into the form of a circle 4 cm in diameter, and about 100 *Dermatophagoides farinae* were released onto the surface of the cut out sheet. After one day, the numbers of dead and alive mites and the number of mites trapped by the adhesive material coated along the edge of the sheet to prevent escape were examined. The total number of the dead mites and trapped mites was defined as the effective control number, from which the percentage of control was determined.

Resultantly, the compound 18, 29, 30, 121, 130 and 133 of this invention respectively showed a percentage of control of 100%. In contrast, the untreated group showed a percentage of control of 5%.

What is claimed is:
1. An ester compound of the formula:

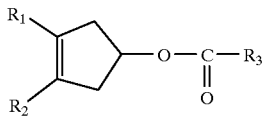

wherein $R_1$ and $R_2$ are the same or different from each other and each represents a hydrogen atom, a halogen atom, a $C_1$–$C_6$ alkyl group optionally substituted with one or more halogen atoms, a $C_2$–$C_6$ alkenyl group optionally substituted with one or more halogen atoms, a $C_2$–$C_6$ alkynyl group optionally substituted with one or more halogen atoms, a $C_3$–$C_7$ cycloalkyl group optionally substituted with one or more halogen atoms, a $C_3$–$C_7$ cycloalkenyl group optionally substituted with one or more halogen atoms, a ($C_3$–$C_6$ cycloalkyl) methyl group optionally substituted with one or more halogen atoms, a benzyl group optionally substituted with one or more halogen atoms, a phenyl group optionally substituted with one or more halogen atoms, or a ($C_1$–$C_6$ alkoxy)methyl group optionally substituted with one or more halogen atoms, and $R_3$ represents a group of the formula:

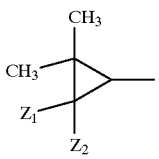

wherein $Z_1$ represents a hydrogen atom or a methyl group, and $Z_2$ represents a hydrogen atom, a $C_1$–$C_6$ alkyl group optionally substituted with one or more halogen atoms, a $C_1$–$C_6$ alkoxy group optionally substituted with one or more halogen atoms, a ($C_1$–$C_6$ alkoxy)methyl group optionally substituted with one or more halogen atoms, a $C_2$–$C_4$ alkenyloxy group optionally substituted with one or more halogen atoms, a ($C_2$–$C_4$ alkenyloxy)methyl group optionally substituted with one or more halogen atoms, or a ($C_3$–$C_4$ alkynyloxy)methyl group optionally substituted with one or more halogen atoms, a group of the formula:

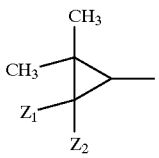

wherein $Z_1$ represents a hydrogen atom or a methyl group, and $Z_2$ represents a group of the formula:

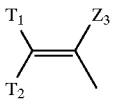

wherein $Z_3$ represents a hydrogen atom or a halogen atom, $T_1$ and $T_2$ are the same or different from each other and each represents a hydrogen atom a halogen atom, a cyano group, a $C_1$–$C_3$ alkyl group optionally substituted with one or more halogen atoms, or a phenyl group optionally substituted with one or more halogen atoms or $T_1$ and $T_2$ conjointly represent a $(CH_2)_n$ group wherein n is an integer of 2 to 5, a group of the formula:

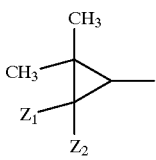

wherein $Z_1$ represents a hydrogen atom or a methyl group, and $Z_2$ represents a group of the formula:

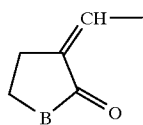

wherein B represents an oxygen atom or a sulfur atom, a group of the formula:

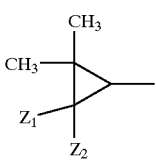

wherein $Z_1$ represents a hydrogen atom or a methyl group, and $Z_2$ represents a group of the formula:

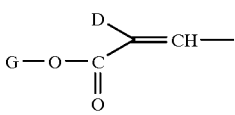

wherein D represents a hydrogen atom or a halogen atom, and G represents a $C_1$–$C_6$ alkyl group optionally substituted with one or more halogen atoms, a $C_3$–$C_5$ cycloalkyl group, or a phenyl group optionally substituted with one or more halogen atoms, or a group of the formula:

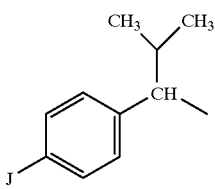

wherein J represents a halogen atom, a $C_{1-6}$ alkyl group optionally substituted with one or more halogen atoms, or a $C_1$–$C_6$ alkoxy group optionally substituted with one or more halogen atoms.

2. The ester compound according to claim 1, wherein $R_1$ represents a $C_1$–$C_6$ alkyl group optionally substituted with one or more halogen atoms, a $C_2$–$C_6$ alkenyl group optionally substituted with one or more halogen atoms, or a $C_2$–$C_6$ alkynyl group optionally substituted with one or more halogen atoms, and $R_2$ represents a hydrogen atom or a $C_1$–$C_6$ alkyl group optionally substituted with one or more halogen atoms.

3. The ester compound according to claim 1, wherein $R_3$ represents a group of the formula:

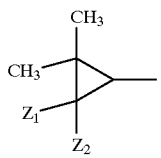

wherein $Z_1$ represents a hydrogen atom or a methyl group, and $Z_2$ represents a hydrogen atom, a $C_1$–$C_6$ alkyl group optionally substituted with one or more halogen atoms, a $C_1$–$C_6$ alkoxy group optionally substituted with one or more halogen atoms, a ($C_1$–$C_6$ alkoxy)methyl group optionally substituted with one or more halogen atoms, a $C_2$–$C_4$ alkenyloxy group optionally substituted with one or more halogen atoms, a ($C_2$–$C_4$ alkenyloxy)methyl group optionally substituted with one or more halogen atoms, or a ($C_3$–$C_4$ alkynyloxy)methyl group optionally substituted with one or more halogen atoms.

4. The ester compound according to claim 1, wherein $R_3$ represents a group of the formula:

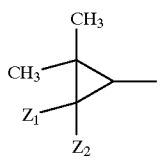

wherein $Z_1$ represents a hydrogen atom or a methyl group, and $Z_2$ represents a group of the formula:

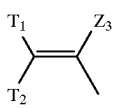

wherein $Z_3$ represents a hydrogen atom or a halogen atom, $T_1$ and $T_2$ are the same or different from each other and each represent a hydrogen atom, a halogen atom, a cyano group, a $C_1$–$C_3$ alkyl group optionally substituted with one or more halogen atoms, or a phenyl group optionally substituted with one or more halogen atoms, or $T_1$ and $T_2$ conjointly represent a $(CH_2)_n$ group, wherein n is an integer of 2 to 5.

5. The ester compound according to claim 1, wherein $R_3$ represents a group of the formula:

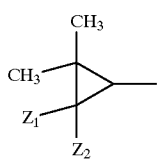

wherein $Z_1$ represents a hydrogen atom or a methyl group, and $Z_2$ represents a group of the formula:

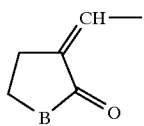

wherein B represents an oxygen atom or a sulfur atom.

6. The ester compound according to claim 1, wherein $R_3$ represents a group of the formula:

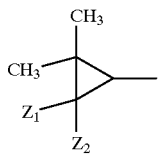

wherein $Z_1$ represents a hydrogen atom or a methyl group, and $Z_2$ represents a group of the formula:

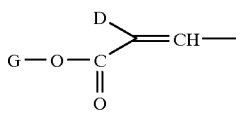

wherein D represents a hydrogen atom or a halogen atom, and G represents a $C_1$–$C_6$ alkyl group optionally substituted with one or more halogen atoms, a $C_3$–$C_5$ cycloalkyl group, or a phenyl group optionally substituted with one or more halogen atoms.

7. The ester compound according to claim 1, wherein $R_3$ represents a group of the formula:

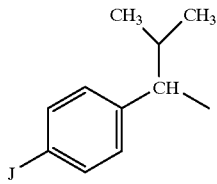

wherein J represents a halogen atom, a $C_1$–$C_6$ alkyl group optionally substituted with one or more halogen atoms, or a $C_1$–$C_6$ alkoxy group optionally substituted with one or more halogen atoms.

8. An arthropod-controlling composition which comprises an effective amount of the ester compound according to claim 1 and an inert carrier.

9. A method for controlling harmful arthropods which comprises applying the ester compound according to claim 1 to a harmful arthropod or to the locus the harmful arthropod inhabits.

10. A method for controlling an insect and/or a pest of Acarina which comprises applying the ester compound according to claim 1 to the insect and/or the pest of Acarina or to the locus the insect and/or the pest of Acarina inhabit.

11. The ester compound according to claim 1, which is (RS)-3-allyl-3-cyclopentenyl 2,2,3,3-tetramethylcyclopropanecarboxylate.

12. The ester compound according to claim 1, which is (RS)-3-propargyl-3-cyclopentenyl 2,2,3,3-tetramethylcyclopropanecarboxylate.

13. The ester compound according to claim 1, which is (RS)-3-(2,2,2-trifluoroethyl)-3-cyclopentenyl 2,2,3,3-tetramethylcyclopropanecarboxylate.

14. The ester compound according to claim 1, which is (RS)-3-allyl-3-cyclopentenyl 1R-trans-3-(2,2-dichlorovinyl)-2,2-dimethylcyclopropanecarboxylate.

15. The ester compound according to claim 1, which is (RS)-3-propyl-3-cyclopentenyl 1R-trans-3-(2,2-dichlorovinyl)-2,2-dimethylcyclopropanecarboxylate.

16. The ester compound according to claim 1, which is (RS)-3-allyl-3-cyclopentenyl 1R-trans-2,2-dimethyl-3-(2-methyl-1-propenyl)cyclopropanecarboxylate.

17. The ester compound according to claim 1, which is (RS)-3-allyl-3-cyclopentenyl 1R-cis-2,2-dimethyl-3-(2-methyl-1-propenyl)cyclopropanecarboxylate.

18. The ester compound according to claim 1, which is (RS)-3-propargyl-3-cyclopentenyl 1R-trans-2,2-dimethyl-3-(2-methyl-1-propenyl)cyclopropranecarboxylate.

19. The ester compound according to claim 1, which is (RS)-3-propargyl-3-cyclopentenyl 1R-cis-2,2-dimethyl-3-(2-methyl-1-propenyl)cyclopropanecarboxylate.

20. The ester compound according to claim 1, which is (RS)-3-propyl-3-cyclopentenyl 1R-trans-2,2-dimethyl-3-(2-methyl-1-propenyl)cyclopropanecarboxylate.

* * * * *